US010801020B2

United States Patent
Yang et al.

(10) Patent No.: US 10,801,020 B2
(45) Date of Patent: *Oct. 13, 2020

(54) HEXURONATE C4-EPIMERASE VARIANT HAVING IMPROVED D-TAGATOSE CONVERSION ACTIVITY, AND D-TAGATOSE PRODUCTION METHOD USING SAME

(71) Applicant: CJ CHEILJEDANG CORPORATION, Seoul (KR)

(72) Inventors: Sung Jae Yang, Suwon (KR); Young Mi Lee, Suwon (KR); Il Hyang Park, Suwon (KR); Chan-Hyoung Lee, Suwon (KR); Hyun Kug Cho, Seoul (KR); Seong Bo Kim, Seongnam (KR); Yang Hee Kim, Suwon (KR); Seung Won Park, Yongin (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/781,676

(22) PCT Filed: Jul. 31, 2017

(86) PCT No.: PCT/KR2017/008243
§ 371 (c)(1),
(2) Date: Jun. 5, 2018

(87) PCT Pub. No.: WO2018/021895
PCT Pub. Date: Feb. 1, 2018

(65) Prior Publication Data
US 2019/0112589 A1    Apr. 18, 2019

(30) Foreign Application Priority Data
Jul. 29, 2016  (KR) .......................... 10-2016-0097500

(51) Int. Cl.
*C12N 9/90* (2006.01)
*C12P 19/02* (2006.01)
*C12P 19/24* (2006.01)

(52) U.S. Cl.
CPC ................ *C12N 9/90* (2013.01); *C12P 19/02* (2013.01); *C12P 19/24* (2013.01); *C12Y 501/02* (2013.01)

(58) Field of Classification Search
None
See application file for complete search history.

(56) References Cited

U.S. PATENT DOCUMENTS

| 10,196,626 B2* | 2/2019 | Yang ........................ C12P 19/02 |
| 2016/0138053 A1* | 5/2016 | Yang .......................... C12P 7/26 |
| | | 435/148 |
| 2017/0306370 A1* | 10/2017 | Kim ........................ C12P 19/02 |

FOREIGN PATENT DOCUMENTS

| JP | 2018521653 A | 8/2018 | |
| KR | 10-2014-0143109 A | 12/2014 | |
| KR | 101480422 B1 | 1/2015 | |
| KR | 1020150059063 A | 5/2015 | |
| KR | 10-2016-0047361 A | 5/2016 | |
| KR | 101638024 B1 | 7/2016 | |
| KR | 10-2017-0015250 A | 2/2017 | |
| WO | WO-2016064146 A1 * | 4/2016 | .............. C12P 19/02 |
| WO | WO-2017018863 A1 * | 2/2017 | ............... C12N 1/20 |

OTHER PUBLICATIONS

Hye-Jung Kim et al., "Novel Activity of UDP-Galactose-4-Epimerase for Free Monosaccharide and Activity Improvement by Active Site-Saturation Mutagenesis", Applied Biochemistry and Biotechnology, 2011, pp. 444-451, vol. 163.
NCBI, GenBank asccession No. WP_015918744.1, May 21, 2013.
Irina A. Rodionova et al., "Tagaturonate-fructuronate epimerase UxaE, a novel enzyme in the hexuronate catabolic network in Thermotoga maritima", Environmental Microbiology, Jul. 23, 2012, pp. 2920-2934, vol. 14, No. 11, Society for Applied Microbiology and Blackwell Publishing Ltd.
International Search Report for International Patent Application No. PCT/KR2017/008243, dated Dec. 15, 2017.
WP_015918744, "D-tagaturonate epimerase UxaE [Thermotoga neapolitanal]"; Protein-NCBI; 2018; 1 page.
European Search Report and Written Opinion for Patent Application No. EP17834835, dated May 11, 2020.
Kivisto, A. et al., "Novel D-tagaturonate epimerase", Jan. 20, 2016, XP055688969, Retrieved from the Internet: URL:https://www.uniprot.org/uniprot/M5DZOO.txt?version=7.

\* cited by examiner

*Primary Examiner* — Robert B Mondesi
*Assistant Examiner* — Todd M Epstein

(57) ABSTRACT

Provided are a hexuronate C4-epimerase variant with improved activity in converting D-fructose by D-tagatose of hexuronate C4-epimerase and a method for production of D-tagatose using them.

15 Claims, No Drawings
Specification includes a Sequence Listing.

HEXURONATE C4-EPIMERASE VARIANT HAVING IMPROVED D-TAGATOSE CONVERSION ACTIVITY, AND D-TAGATOSE PRODUCTION METHOD USING SAME

CROSS-REFERENCE TO RELATED APPLICATIONS

The present specification is a U.S. National Stage of International Patent Application No. PCT/KR2017/008243 filed Jul. 31, 2017, which claims priority to and the benefit of Korean Patent Application No. 10-2016-0097500 filed in the Korean Intellectual Property Office on Jul. 29, 2016, the entire contents of which are incorporated herein by reference.

TECHNICAL FIELD

The present invention relates to a hexuronate C4-epimerase variant with improved conversion activity to D-tagatose and a method for production of D-tagatose using them.

BACKGROUND ART

Tagatose is a natural sweetener that is present in small amounts in foods such as milk, cheese, cacao, etc., and sweet and natural fruits such as apples and tangerines, and also has physical properties similar to those of sugar. Tagatose has a calorie of 1.5 kcal/g, which is about one-third of sugar, and has a glycemic index (GI) of 3, which is about 5% of the sugar. Tagatose has a variety of health functionalities with sweetness similar to sugar, and thus, tagatose may be used as a substitute sweetener capable of satisfying health and taste at the same time when applied to various products.

Conventionally known methods for production of tagatose include a chemical (catalytic reaction) method and a biological (isomerization enzyme reaction) method using galactose as a main raw material (see Korean Patent Laid-Open Publication No. 2009-0082774). However, lactose, which is a basic raw material of galactose in the above-described production method, is unstable in price due to a production amount, demand and a supply amount of raw milk and lactose in the international market, and thus there is a limit to stably meet supply and demand of raw materials for production of tagatose. Therefore, a new method in which tagatose is able to be produced by using common generic sugars (sugar, glucose, fructose, etc.) as raw materials has been demanded. Accordingly, the present inventors have reported a production method for tagatose from fructose using a novel hexuronate C4-epimerase (Korean Patent Laid-Open Publication No. 10-2014-0143109). However, for industrial production, it is necessary to develop an enzyme having higher conversion activity to tagatose.

Under these circumstances, the present inventors confirmed that when an amino acid at a specific position of the hexuronate C4-epimerase was mutated, the conversion activity from fructose to tagatose was remarkably increased as compared to that of the wild-type, and completed the present invention.

Throughout the present specification, a number of patents and documents are referenced and the citation is shown in parentheses. The disclosures of these patents and publications are hereby incorporated by reference in their entirety to more clearly illustrate the present invention and the level of the technical field in which the invention pertains.

Disclosure

The Sequence Listing created on Jun. 5, 2018 with a file size of 5 KB, and filed herewith in ASCII text file format as the file entitled "40I4148.TXT," is hereby incorporated by reference in its entirety.

Technical Problem

An object of the present invention is to provide a hexuronate C4-epimerase variant in which a tyrosine (Y)-403 amino acid residue from N-terminal of a hexuronate C4-epimerase consisting of an amino acid sequence of SEQ ID NO: 1 is mutated.

Another object of the present invention is to provide a hexuronate C4-epimerase variant in which a threonine (T)-272 amino acid residue from N-terminal of a hexuronate C4-epimerase consisting of an amino acid sequence of SEQ ID NO: 1 is mutated.

Still another object of the present invention is to provide a hexuronate C4-epimerase variant in which a serine (S)-185 amino acid residue from N-terminal of a hexuronate C4-epimerase consisting of an amino acid sequence of SEQ ID NO: 1 is mutated.

Still another object of the present invention is to provide a hexuronate C4-epimerase variant in which a leucine (L)-77 amino acid residue from N-terminal of a hexuronate C4-epimerase consisting of an amino acid sequence of SEQ ID NO: 1 is mutated.

Still another object of the present invention is to provide a hexuronate C4-epimerase variant in which an alanine (A)-158 amino acid residue from N-terminal of a hexuronate C4-epimerase consisting of an amino acid sequence of SEQ ID NO: 1 is mutated.

Still another object of the present invention is to provide a hexuronate C4-epimerase variant in which a proline (P)-351 amino acid residue from N-terminal of a hexuronate C4-epimerase consisting of an amino acid sequence of SEQ ID NO: 1 is mutated.

Still another object of the present invention is to provide a hexuronate C4-epimerase variant in which serine (S)-125, lysine (K)-164, aspartic acid (D)-168, and glutamic acid (E)-175 amino acid residues from N-terminal of a hexuronate C4-epimerase consisting of an amino acid sequence of SEQ ID NO: 1 are mutated.

Still another object of the present invention is to provide a hexuronate C4-epimerase variant in which serine (S)-125, glutamine (Q)-149, and valine (V)-267 amino acid residues from N-terminal of a hexuronate C4-epimerase consisting of an amino acid sequence of SEQ ID NO: 1 are mutated.

Still another object of the present invention is to provide a nucleic acid encoding a hexuronate C4-epimerase variant disclosed herein, a transformant including the nucleic acid, a microorganism expressing the variant of the present invention or a culture thereof, or a composition for producing D-tagatose comprising the hexuronate C4-epimerase variant of the present invention.

Still another object of the present invention is to provide a method for production of D-tagatose comprising contacting the hexuronate C4-epimerase variant of the present invention, a transformant of the present invention, a microorganism expressing the variant of the present invention or a culture thereof, or a composition for producing tagatose of the present invention, with D-fructose.

Hereinafter, the present invention is described in more detail. Other objects and advantages of the present invention are more apparent from the following detailed description together with the appended claims. Descriptions that are not described in the specification can be sufficiently recognized and deduced by a person skilled in the technical field or fields similar to this, details thereof are omitted.

Technical Solution

In order to accomplish the object of the present invention, according to an exemplary embodiment of the present invention, there is provided a hexuronate C4-epimerase variant in which one or more amino acid residues selected from the group consisting of histidine (H)-9, tyrosine (Y)-21, glutamic acid (E)-60, valine (V)-62, glutamic acid (E)-68, leucine (L)-77, leucine (L)-91, threonine (T)-97, serine (S)-125, valine (V)-126, leucine (L)-140, aspartic acid (D)-141, tryptophan (W)-145, glutamine (Q)-149, glycine (G)-157, alanine (A)-158, alanine (A)-160, valine (V)-163, lysine (K)-164, proline (P)-166, glutamic acid (E)-167, aspartic acid (D)-168, glutamic acid (E)-175, glycine (G)-176, phenylalanine (F)-177, serine (S)-185, methionine (M)-202, glycine (G)-218, tyrosine (Y)-221, aspartic acid (D)-231, valine (V)-241, tyrosine (Y)-242, valine (V)-267, serine (S)-268, threonine (T)-272, threonine (T)-276, valine (V)-284, phenylalanine (F)-295, phenylalanine (F)-297, phenylalanine (F)-302, tryptophan (W)-306, leucine (L)-316, lysine (K)-337, proline (P)-351, phenylalanine (F)-361, alanine (A)-366, arginine (R)-386, isoleucine (I)-388, serine (S)-402, tyrosine (Y)-403, valine (V)-415, aspartic acid (D)-429, tyrosine (Y)-440, and glycine (G)-441 from N-terminal of hexuronate C4-epimerase consisting of an amino acid sequence of SEQ ID NO: 1 are mutated to other amino acid residues [see Tables 2 to 10].

According to another exemplary embodiment of the present invention, there is provided a hexuronate C4-epimerase variant in which a tyrosine (Y)-403 amino acid residue from N-terminal of a hexuronate C4-epimerase consisting of an amino acid sequence of SEQ ID NO: 1 is mutated.

The tyrosine (Y)-403 amino acid residue may be substituted with alanine (A), cysteine (C), aspartic acid (D), glutamic acid (E), phenylalanine (F), glycine (G), histidine (H), isoleucine (I), lysine (K), leucine (L), methionine (M), asparagine (N), proline (P), glutamine (Q), arginine (R), serine (S), threonine (T), valine (V) or tryptophan (W), and more specifically, may be substituted with phenylalanine (F), serine (S), threonine (T), glutamine (Q), valine (V), alanine (A), or isoleucine (I).

In an exemplary embodiment, in the hexuronate C4-epimerase variant of the present invention, a serine (S)-125 amino acid residue from the N-terminal of the hexuronate C4-epimerase consisting of an amino acid sequence of SEQ ID NO: 1 may additionally be mutated in addition to the position No. 403. The serine (S)-125 amino acid residue may be substituted with aspartic acid (D), glutamine (Q), glutamic acid (E), threonine (T), asparagine (N), cysteine (C), or tyrosine (Y). In an example of the exemplary embodiment, the hexuronate C4-epimerase variant of the present invention may be a variant in which the tyrosine (Y)-403 amino acid residue is substituted with phenylalanine (F), serine (S), threonine (T), glutamine (Q), or valine (V), and the serine (S)-125 amino acid residue is substituted with aspartic acid (D).

In an example of the exemplary embodiment, the hexuronate C4-epimerase variant of the present invention may be a variant in which one or more amino acid residues selected from the group consisting of serine (S)-185, valine (V)-267, serine (S)-268, threonine (T)-272, tryptophan (W)-306, and arginine (R)-386 from the N-terminal of the hexuronate C4-epimerase consisting of the amino acid sequence of SEQ ID NO: 1 may additionally be mutated in addition to the tyrosine (Y)-403 amino acid residue and the serine (S)-125 amino acid residue. The serine (S)-185 may be substituted with lysine (K), arginine (R), histidine (H), glutamine (Q), alanine (A) or glycine (G); the valine (V)-267 may be substituted with methionine (M); the serine (S)-268 may be substituted with cysteine (C) or threonine (T); the threonine (T)-272 may be substituted with alanine (A), aspartic acid (D), glutamic acid (E), phenylalanine (F), glycine (G), histidine (H), isoleucine (I), lysine (K), leucine (L), methionine (M), asparagine (N), proline (P), glutamine (Q), arginine (R), serine (S), valine (V) or tyrosine (Y); the tryptophan (W)-306 may be substituted with phenylalanine (F), histidine (H), methionine (M) or valine (V); the arginine (R)-386 may be substituted with proline (P) or valine (V).

In an example of the exemplary embodiment, the present invention may provide a variant which is mutated at any one position of the serine (S)-185, the valine (V)-267, the serine (S)-268, the threonine (T)-272, the tryptophan (W)-306, and the arginine (R)-386, in addition to the mutations of the tyrosine (Y)-403 amino acid residue and the serine (S)-125 amino acid residue. For example, the hexuronate C4-epimerase variant of the present invention may be a variant in which the tyrosine (Y)-403 amino acid residue is substituted with phenylalanine (F), serine (S), threonine (T), glutamine (Q), valine (V), alanine (A), or isoleucine (I), the serine (S)-125 amino acid residue is substituted with aspartic acid (D), and the serine (S)-185 amino acid residue is substituted with lysine (K), histidine (H), or glutamine (Q). In an example, the hexuronate C4-epimerase variant of the present invention may be a variant in which the tyrosine (Y)-403 amino acid residue is substituted with phenylalanine (F), serine (S), threonine (T), glutamine (Q), valine (V), alanine (A), or isoleucine (I), the serine (S)-125 amino acid residue is substituted with aspartic acid (D), and the valine (V)-267 amino acid residue is substituted with methionine (M). In an example, the hexuronate C4-epimerase variant of the present invention may be a variant in which the tyrosine (Y)-403 amino acid residue is substituted with phenylalanine (F), serine (S), threonine (T), glutamine (Q), valine (V), alanine (A), or isoleucine (I), the serine (S)-125 amino acid residue is substituted with aspartic acid (D), and the serine (S)-268 amino acid residue is substituted with cysteine (C) or threonine (T). In an example, the hexuronate C4-epimerase variant of the present invention may be a variant in which the tyrosine (Y)-403 amino acid residue is substituted with phenylalanine (F), serine (S), threonine (T), glutamine (Q), valine (V), alanine (A), or isoleucine (I), the serine (S)-125 amino acid residue is substituted with aspartic acid (D), and the threonine (T)-272 amino acid residue is substituted with aspartic acid (D). In an example, the hexuronate C4-epimerase variant of the present invention may be a variant in which the tyrosine (Y)-403 amino acid residue is substituted with phenylalanine (F), serine (S), threonine (T), glutamine (Q), valine (V), alanine (A), or isoleucine (I), the serine (S)-125 amino acid residue is substituted with aspartic acid (D), and the tryptophan (W)-306 amino acid residue is substituted with phenylalanine (F), histidine (H), methionine (M) or valine (V). In an example, the hexuronate C4-epimerase variant of the present invention may be a variant in which the tyrosine (Y)-403 amino acid residue is substituted with phenylalanine (F), serine (S), threonine (T), glutamine (Q), valine (V), alanine (A), or isoleucine (I), the serine (S)-125 amino acid residue is substituted with aspartic acid (D), and the arginine (R)-386 amino acid residue is substituted with proline (P) or valine (V).

In another example of the exemplary embodiment, the hexuronate C4-epimerase variant of the present invention may be a variant which is substituted at any two positions selected from the serine (S)-185, the valine (V)-267, the serine (S)-268, the threonine (T)-272, the tryptophan (W)-306, and the arginine (R)-386, in addition to the tyrosine (Y)-403 amino acid residue and the serine (S)-125 amino acid residue. The mutation position may be positions at 185 and 267, positions at 185 and 268, positions at 185 and 272, positions at 185 and 306, positions at 185 and 386, positions at 267 and 268, positions at 267 and 272, positions at 267 and 306, positions at 267 and 386, positions at 268 and 272, positions at 268 and 306, positions at 268 and 386, positions at 272 and 306, positions at 272 and 386, or positions at 306 and 386. For example, the hexuronate C4-epimerase variant of the present invention may be a variant in which the tyrosine (Y)-403 amino acid residue is substituted with phenylalanine (F), serine (S), threonine (T), glutamine (Q), valine (V), alanine (A), or isoleucine (I), the serine (S)-125 amino acid residue is substituted with aspartic acid (D), the serine (S)-185 amino acid residue is substituted with lysine (K), histidine (H), or glutamine (Q), and the valine (V)-267 is substituted with methionine (M). In an example, the hexuronate C4-epimerase variant of the present invention may be a variant in which the tyrosine (Y)-403 amino acid residue is substituted with phenylalanine (F), serine (S), threonine (T), glutamine (Q), valine (V), alanine (A), or isoleucine (I), the serine (S)-125 amino acid residue is substituted with aspartic acid (D), the serine (S)-185 amino acid residue is substituted with lysine (K), histidine (H), or glutamine (Q), and the serine (S)-268 amino acid residue is substituted with cysteine (C) or threonine (T). In an example, the hexuronate C4-epimerase variant of the present invention may be a variant in which the tyrosine (Y)-403 amino acid residue is substituted with phenylalanine (F), serine (S), threonine (T), glutamine (Q), valine (V), alanine (A), or isoleucine (I), the serine (S)-125 amino acid residue is substituted with aspartic acid (D), the serine (S)-185 amino acid residue is substituted with lysine (K), histidine (H), or glutamine (Q), and the threonine (T)-272 is substituted with aspartic acid (D). In an example, the hexuronate C4-epimerase variant of the present invention may be a variant in which the tyrosine (Y)-403 amino acid residue is substituted with phenylalanine (F), serine (S), threonine (T), glutamine (Q), valine (V), alanine (A), or isoleucine (I), the serine (S)-125 amino acid residue is substituted with aspartic acid (D), the serine (S)-268 amino acid residue is substituted with cysteine (C) or threonine (T), and the tryptophan (W)-306 is substituted with phenylalanine (F), histidine (H), methionine (M) or valine (V). In an example, the hexuronate C4-epimerase variant of the present invention may be a variant in which the tyrosine (Y)-403 amino acid residue is substituted with phenylalanine (F), serine (S), threonine (T), glutamine (Q), valine (V), alanine (A), or isoleucine (I), the serine (S)-125 amino acid residue is substituted with aspartic acid (D), the serine (S)-268 amino acid residue is substituted with cysteine (C) or threonine (T), and the arginine (R)-386 amino acid residue is substituted with proline (P) or valine (V).

In another example of the exemplary embodiment, the hexuronate C4-epimerase variant of the present invention may be a variant which is substituted at any three positions selected from the serine (S)-185, the valine (V)-267, the threonine (T)-272, the tryptophan (W)-306, and the arginine (R)-386, in addition to the tyrosine (Y)-403 amino acid residue and the serine (S)-125 amino acid residue. The mutation position may be, for example, the positions at 185, 267, and 268; the positions at 185, 267, and 272; the positions at 185, 267, and 306; the positions at 185, 267, and 386; the positions at 185, 268, and 272; the positions at 185, 268, and 306; the positions at 185, 268, and 386; the positions at 185, 272, and 306; the positions at 185, 272, and 386; the positions at 267, 268, and 272; the positions at 267, 268, and 306; the positions at 267, 268, and 386; the positions at 267, 272, and 306; the positions at 267, 272, and 386; the positions at 267, 386, and 306; the positions at 268, 272, and 306; the positions at 268, 272, and 386; the positions at 268, 306, and 386; or the positions at 272, 306, and 386. In an example, the hexuronate C4-epimerase variant of the present invention may be a variant in which the tyrosine (Y)-403 amino acid residue is substituted with phenylalanine (F), serine (S), threonine (T), glutamine (Q), valine (V), alanine (A), or isoleucine (I), the serine (S)-125 amino acid residue is substituted with aspartic acid (D), the serine (S)-185 amino acid residue is substituted with lysine (K), histidine (H), or glutamine (Q), the valine (V)-267 amino acid residue is substituted with methionine (M), and the serine (S)-268 amino acid residue is substituted with cysteine (C) or threonine (T). For example, the hexuronate C4-epimerase variant of the present invention may be a variant in which the tyrosine (Y)-403 amino acid residue is substituted with phenylalanine (F), serine (S), threonine (T), glutamine (Q), valine (V), alanine (A), or isoleucine (I), the serine (S)-125 amino acid residue is substituted with aspartic acid (D), the serine (S)-185 amino acid residue is substituted with lysine (K), histidine (H), or glutamine (Q), the valine (V)-267 amino acid residue is substituted with methionine (M), and the threonine (T)-272 is substituted with aspartic acid (D). For example, the hexuronate C4-epimerase variant of the present invention may be a variant in which the tyrosine (Y)-403 amino acid residue is substituted with phenylalanine (F), serine (S), threonine (T), glutamine (Q), valine (V), alanine (A), or isoleucine (I), the serine (S)-125 amino acid residue is substituted with aspartic acid (D), the serine (S)-185 amino acid residue is substituted with lysine (K), histidine (H), or glutamine (Q), the valine (V)-267 amino acid residue is substituted with methionine (M), and the tryptophan (W)-306 amino acid residue is substituted with phenylalanine (F), histidine (H), methionine (M) or valine (V).

In another example of the exemplary embodiment, the hexuronate C4-epimerase variant of the present invention may be a variant which is substituted at any four, five or six positions selected from the serine (S)-185, the valine (V)-267, the serine (S)-268, the threonine (T)-272, the tryptophan (W)-306, and the arginine (R)-386, in addition to the tyrosine (Y)-403 amino acid residue and the serine (S)-125 amino acid residue.

In an exemplary embodiment, in the hexuronate C4-epimerase variant of the present invention, the lysine (K)-164, the aspartic acid (D)-168, the glutamic acid (E)-175, the asparagine (N)-297, and the isoleucine (I)-388 from the N-terminal of the hexuronate C4-epimerase consisting of the amino acid sequence of SEQ ID NO: 1 may additionally be mutated in addition to the tyrosine (Y)-403, serine (S)-125, and serine (S)-268 amino acid residues. The lysine (K)-164 may be substituted with methionine (M), the aspartic acid (D)-168 may be substituted with glutamic acid (E), the glutamic acid (E)-175 may be substituted with glycine (G), the asparagine (N)-297 may be substituted with lysine (K), and the isoleucine (I)-388 may be substituted with valine (V). The hexuronate C4-epimerase variant of an example of the exemplary embodiment may be a variant in which the tyrosine (Y)-403 amino acid residue is substituted with phenylalanine (F), serine (S), threonine (T), glutamine (Q), valine (V), alanine (A), or isoleucine (I), the serine (S)-125 amino acid residue is substituted with aspartic acid (D), the serine (S)-268 amino acid residue is substituted with cysteine (C) or threonine (T), and the lysine (K)-164 is substituted with methionine (M), the aspartic acid (D)-168 is substituted with glutamic acid (E), the glutamic acid (E)-175 is substituted with glycine (G), the asparagine (N)-297 is substituted with lysine (K), and the isoleucine (I)-388 is substituted with valine (V).

In an exemplary embodiment, in the hexuronate C4-epimerase variant of the present invention, the proline (P)-351 from the N-terminal of the hexuronate C4-epimerase consisting of the amino acid sequence of SEQ ID NO: 1 may additionally be mutated in addition to the tyrosine (Y)-403, serine (S)-125, valine (V)-267, and arginine (R)-386 amino acid residues. Specifically, the proline (P)-351 may be substituted with serine (S).

In an exemplary embodiment, in the hexuronate C4-epimerase variant of the present invention, the glutamic acid (E)-68 from the N-terminal of the hexuronate C4-epimerase consisting of the amino acid sequence of SEQ ID NO: 1 may additionally be mutated in addition to the tyrosine (Y)-403, serine (S)-125, serine (S)-185, valine (V)-267, and tryptophan (W)-306 amino acid residues. The glutamic acid (E)-68 may be substituted with glycine (G).

In an exemplary embodiment, in the hexuronate C4-epimerase variant of the present invention, the glutamic acid (E)-60, the methionine (M)-202, the tyrosine (Y)-221 and the tyrosine (Y)-242 from the N-terminal of the hexuronate C4-epimerase consisting of the amino acid sequence of SEQ ID NO: 1 may additionally be mutated in addition to the tyrosine (Y)-403, serine (S)-125, valine (V)-267, serine (S)-268, and arginine (R)-386 amino acid residues. The glutamic acid (E)-60 may be substituted with aspartic acid (D), the methionine (M)-202 may be substituted with threonine (T), the tyrosine (Y)-221 may be substituted with phenylalanine (F), and the tyrosine (Y)-242 may be substituted with phenylalanine (F).

In an exemplary embodiment, in the hexuronate C4-epimerase variant of the present invention, one or more amino acid residues selected from the group consisting of the serine (S)-185, the valine (V)-267, the serine (S)-268, the threonine (V)-272, the tryptophan (W)-306, and the arginine (R)-386 may additionally be mutated in addition to the tyrosine (Y)-403 and serine (S)-125 amino acid residues, and in the hexuronate C4-epimerase variant of the present invention, one or more amino acid residues selected from the group consisting of the leucine (L)-91, the aspartic acid (D)-141 and the glycine (G)-176 from the N-terminal of the hexuronate C4-epimerase consisting of the amino acid sequence of SEQ ID NO: 1 may additionally be mutated. Specifically, in the hexuronate C4-epimerase variant of the present invention, the leucine (L)-91, the aspartic acid (D)-141 or the glycine (G)-176 amino acid residue may additionally be mutated in addition to the tyrosine (Y)-403, serine (S)-125, serine (S)-185, valine (V)-267, serine (S)-268 and threonine (T)-272 amino acid residues. The leucine (L)-91 may be substituted with tryptophan (W), isoleucine (I), or asparagine (N), the aspartic acid (D)-141 may be substituted with phenylalanine (F), and the glycine (G)-176 may be substituted with histidine (H), phenylalanine (F) or tyrosine (Y).

In an exemplary embodiment, in the hexuronate C4-epimerase variant of the present invention, one or more amino acid residues selected from the group consisting of the valine (V)-267, the serine (S)-268, the threonine (T)-272, and the tryptophan (W)-306 may additionally be mutated in addition to the tyrosine (Y)-403 and the serine (5)-125 amino acid residues, and in the hexuronate C4-epimerase variant, the valine (V)-284 or the valine (V)-415 from the N-terminal of the hexuronate C4-epimerase consisting of the amino acid sequence of SEQ ID NO: 1 may additionally be mutated. Specifically, in the hexuronate C4-epimerase variant of the present invention, the valine (V)-284 and valine (V)-415 amino acid residues may additionally be mutated in addition to the tyrosine (Y)-403, serine (S)-125, valine (V)-267, serine (S)-268, threonine (T)-272, and tryptophan (W)-306 amino acid residues. The valine (V)-284 may be substituted with alanine (A), and the valine (V)-415 may be substituted with glutamic acid (E).

In an exemplary embodiment, in the hexuronate C4-epimerase variant of the present invention, one or more amino acid residues selected from the group consisting of the serine (S)-185, the valine (V)-267, the serine (S)-268, the threonine (V)-272, and the tryptophan (W)-306 may additionally be mutated in addition to the tyrosine (Y)-403 and serine (S)-125 amino acid residues, and in the hexuronate C4-epimerase variant, the proline (P)-166 or the aspartic acid (D)-231 from the N-terminal of the hexuronate C4-epimerase consisting of the amino acid sequence of SEQ ID NO: 1 may additionally be mutated. Specifically, in the hexuronate C4-epimerase variant of the present invention, the proline (P)-166 or the aspartic acid (D)-231 may additionally be mutated in addition to the tyrosine (Y)-403, serine (S)-125, serine (S)-185, valine (V)-267, serine (S)-268, threonine (T)-272, and tryptophan (W)-306 amino acid residues. The proline (P)-166 may be substituted with arginine (R), and the aspartic acid (D)-231 may be substituted with arginine (R).

In an exemplary embodiment, in the hexuronate C4-epimerase variant of the present invention, the serine (S)-185, valine (V)-267, serine (S)-268, threonine (V)-272, the tryptophan (W) residue at position 306 and the arginine (R) residue at position 386 may additionally be mutated in addition to the tyrosine (Y)-403 and serine (S)-125 amino acid residues, and in the hexuronate C4-epimerase variant, the valine (V)-126 from the N-terminal of the hexuronate C4-epimerase consisting of the amino acid sequence of SEQ ID NO: 1 may additionally be mutated. Specifically, in the hexuronate C4-epimerase variant of the present invention, the valine (V)-126 may additionally be mutated in addition to the tyrosine (Y)-403, serine (S)-125, serine (S)-185, valine (V)-267, serine (S)-268, threonine (T)-272, and tryptophan (W)-386 amino acid residues. The valine (V)-126 may be substituted with alanine (A), phenylalanine (F), glycine (G), isoleucine (I), leucine (L), proline (P), asparagine (R) or threonine (T).

According to an exemplary embodiment of the present invention, the hexuronate C4-epimerase variant of the present invention may be a hexuronate C4-epimerase variant in which the tyrosine (Y)-403, serine (S)-125, serine (5)-185, valine (V)-267, serine (S)-268, threonine (T)-272, tryptophan (W)-306, and arginine (R)-386 amino acid residues from the N-terminal of the hexuronate C4-epimerase consisting of the amino acid sequence of SEQ ID NO: 1 are mutated.

In an exemplary embodiment, in the hexuronate C4-epimerase variant of the present invention, the threonine (T)-97, the valine (V)-126, the tryptophan (W)-145, the valine (V)-163, the lysine (K)-164, the proline (P)-166, the aspartic acid (D)-231, the valine (V)-241, the threonine (T)-276, the lysine (K)-337, the alanine (A)-366, the serine (S)-402, the aspartic acid (D)-429 or the tyrosine (Y)-440 amino acid residue may additionally be mutated in addition to the tyrosine (Y)-403, serine (S)-125, serine (S)-185, valine (V)-267, serine (S)-268, threonine (T)-272, and arginine (R)-386 amino acid residues of SEQ ID NO: 1. The threonine (T)-97 may be substituted with alanine (A) or leucine (L); the valine (V)-126 may be substituted with phenylalanine (F), leucine (L), proline (P), isoleucine (I), threonine (T), alanine (A), glycine (G) or arginine (R); the tryptophan (W)-145 may be substituted with alanine (A); the valine (V)-163 may be substituted with alanine (A), methionine (M) or glutamine (Q); the lysine (K)-164 may be substituted with methionine (M); the proline (P)-166 may be substituted with arginine (R); the aspartic acid (D)-231 may be substituted with arginine (R); the valine (V)-241 may be substituted with asparagine (N), threonine (T) or serine (S); the threonine (T)-276 may be substituted with glutamic acid (E) or alanine (A); the lysine (K)-337 may be substituted with glutamic acid (E), phenylalanine (F), asparagine (N), proline (P), serine (S), threonine (T), tryptophan (W) or tyrosine (Y); the alanine (A)-366 may be substituted with serine (S), glycine (G) or cysteine (C); the serine (S)-402 may be substituted with phenylalanine (F), cysteine (C) or tyrosine (Y); the aspartic acid (D)-429 may be substituted with proline (P), and the tyrosine (Y)-440 may be substituted with alanine (A).

In an exemplary embodiment, in the hexuronate C4-epimerase variant of the present invention, the lysine (K)-164, the aspartic acid (D)-166 or the aspartic acid (D)-231 amino acid residue from the N-terminal of the hexuronate C4-epimerase consisting of the amino acid sequence of SEQ ID NO: 1 may additionally be mutated in addition to the tyrosine (Y)-403, serine (S)-125, serine (S)-185, valine (V)-267, serine (S)-268, threonine (T)-272, arginine (R) tryptophan (W) 386, and threonine (T)-97 amino acid residues. The lysine (K)-164 may be substituted with methionine (M); the aspartic acid (D)-166 may be substituted with arginine (R); and the aspartic acid (D)-231 may be substituted with arginine (R).

In an exemplary embodiment, in the hexuronate C4-epimerase variant of the present invention, the aspartic acid (D)-231 amino acid residue from the N-terminal of the hexuronate C4-epimerase consisting of the amino acid sequence of SEQ ID NO: 1 may additionally be mutated in addition to the tyrosine (Y)-403, serine (S)-125, serine (S)-185, valine (V)-267, serine (S)-268, threonine (T)-272, arginine (R)-386, and valine (V)-163 amino acid residues. The aspartic acid (D)-231 may be substituted with arginine (R).

In an exemplary embodiment, in the hexuronate C4-epimerase variant of the present invention, the glycine (G)-157, the alanine (A)-160, the glutamic acid (E)-167, the phenylalanine (F)-177, the glycine (G)-218, the phenylalanine (F)-295, the phenylalanine (F)-302, the phenylalanine (F)-361, the alanine (A)-366 or the glycine (G)-441 amino acid residue from the N-terminal of the hexuronate C4-epimerase consisting of the amino acid sequence of SEQ ID NO: 1 may additionally be mutated in addition to the tyrosine (Y)-403, serine (S)-125, serine (S)-185, valine (V)-267, serine (S)-268, threonine (T)-272, arginine (R)-386, and lysine (K)-337 amino acid residues. The glycine (G)-157 may be substituted with arginine (R); the alanine (A)-160 may be substituted with leucine (L), phenylalanine (F), arginine (R) or tyrosine (Y); the glutamic acid (E)-167 may be substituted with alanine (A), tryptophan (W), isoleucine (I), lysine (K), methionine (M), valine (V) or serine (S); the phenylalanine (F)-177 may be substituted with tyrosine (Y), histidine (H) or leucine (L); the glycine (G)-218 may be substituted with isoleucine (I), serine (S), leucine (L), phenylalanine (F) or cysteine (C); the phenylalanine (F)-295 may be substituted with cysteine (C), arginine (R) or tyrosine (Y); the phenylalanine (F)-302 may be substituted with cysteine (C); the phenylalanine (F)-361 may be substituted with lysine (K), glutamic acid (E), valine (V), tryptophan (W), tyrosine (Y), methionine (M), arginine (R), glutamine (Q), leucine (L) or cysteine (C); the alanine (A)-366 may be substituted with serine (S); the glycine (G)-441 may be substituted with glutamic acid (E), tryptophan (W), histidine (H), lysine (K), alanine (A), arginine (R), serine (S) or phenylalanine (F).

In an exemplary embodiment, in the hexuronate C4-epimerase variant of the present invention, the leucine (L)-77 amino acid residue, the alanine (A)-158 amino acid residue, or a combination of the amino acid residues from the N-terminal of the hexuronate C4-epimerase consisting of the amino acid sequence of SEQ ID NO: 1 may additionally be mutated in addition to the tyrosine (Y)-403 amino acid residue and the serine (S)-125 amino acid residue. The leucine (L)-77 may be substituted with proline (P) or arginine (R), and the alanine (A)-158 may be substituted with threonine (T). In the hexuronate C4-epimerase variant in which the tyrosine (Y)-403, the serine (S)-125, the leucine (L)-77 amino acid residue, and the alanine (A)-158 amino acid residue are mutated, the arginine (R)-386 amino acid residue from the N-terminal of the hexuronate C4-epimerase consisting of the amino acid sequence of SEQ ID NO: 1 may additionally be mutated. The arginine (R)-386 may be substituted with proline (P) or valine (V).

According to another exemplary embodiment of the present invention, there is provided a hexuronate C4-epimerase variant in which a serine (S)-185 amino acid residue from N-terminal of a hexuronate C4-epimerase consisting of an amino acid sequence of SEQ ID NO: 1 is mutated. The serine (S)-185 amino acid residue may be substituted with alanine (A), glycine (G), histidine (H), lysine (K), glutamine (Q), or arginine (R).

In an exemplary embodiment, in the hexuronate C4-epimerase variant of the present invention, the serine (S)-125 amino acid residue may additionally be mutated in addition to the position No. 185. The serine (S)-125 amino acid residue may be substituted with cysteine (C), tyrosine (Y), glutamine (Q), glutamic acid (E), threonine (T), asparagine (N), or aspartic acid (D). In an example of the exemplary embodiment, the hexuronate C4-epimerase variant of the present invention may be a variant in which the serine (S)-185 amino acid residue is substituted with alanine (A), glycine (G), histidine (H), lysine (K), glutamine (Q), or arginine (R), and the serine (S)-125 amino acid residue is substituted with cysteine (C), tyrosine (Y), glutamine (Q), glutamic acid (E), threonine (T), asparagine (N), or aspartic acid (D). In a specific example, the hexuronate C4-epimerase variant of the present invention may be a variant in which the serine (S)-185 amino acid residue is substituted with alanine (A), glycine (G), histidine (H), lysine (K), glutamine (Q), or arginine (R), and the serine (S)-125 amino acid residue is substituted with aspartic acid (D).

In an exemplary embodiment, in the hexuronate C4-epimerase variant of the present invention, the serine (S)-268 amino acid residue from the N-terminal of the hexuronate C4-epimerase consisting of the amino acid sequence of SEQ ID NO: 1 is additionally mutated in addition to the serine (S)-185 and the serine (S)-125. The serine (S)-268 may be substituted with cysteine (C) or threonine (T).

According to another exemplary embodiment of the present invention, there is provided a hexuronate C4-epimerase variant in which the threonine (T)-272 amino acid residue from the N-terminal of a hexuronate C4-epimerase consisting of the amino acid sequence of SEQ ID NO: 1 is mutated. The threonine (T)-272 may be substituted with alanine (A), aspartic acid (D), glutamic acid (E), phenylalanine (F), glycine (G), histidine (H), isoleucine (I), lysine (K), leucine (L), methionine (M), asparagine (N), proline (P), glutamine (Q), arginine (R), serine (S), valine (V) or tyrosine (Y).

In an exemplary embodiment, in the hexuronate C4-epimerase variant of the present invention, the serine (S)-125 amino acid residue may additionally be mutated in addition to the threonine (T)-272 amino acid residue. The serine (S)-125 amino acid residue may be substituted with cysteine (C), tyrosine (Y), glutamine (Q), glutamic acid (E), threonine (T), asparagine (N), or aspartic acid (D). Accordingly, the hexuronate C4-epimerase variant of the present invention may be a variant in which the threonine (T)-272 is substituted with alanine (A), aspartic acid (D), glutamic acid (E), phenylalanine (F), glycine (G), histidine (H), isoleucine (I), lysine (K), leucine (L), methionine (M), asparagine (N), proline (P), glutamine (Q), arginine (R), serine (S), valine (V) or tyrosine (Y), and the serine (S)-125 is substituted with cysteine (C), tyrosine (Y), glutamine (Q), glutamic acid (E), threonine (T), asparagine (N) or aspartic acid (D). In an example, the hexuronate C4-epimerase variant of the present invention may be a variant in which the threonine (T)-272 is substituted with serine (S), proline (P), aspartic acid (D), histidine (H), glutamine (Q), asparagine (N), lysine (K) or tyrosine (Y), and the serine (S)-125 is substituted with aspartic acid (D).

In an exemplary embodiment, in the hexuronate C4-epimerase variant of the present invention, the serine (S)-185 amino acid residue from the N-terminal of the hexuronate C4-epimerase consisting of the amino acid sequence of SEQ ID NO: 1 may additionally be mutated in addition to the threonine (T)-272 and serine (S)-125 amino acid residues. The serine (S)-185 amino acid residue may be substituted with alanine (A), glycine (G), histidine (H), lysine (K), glutamine (Q), or arginine (R). In an exemplary embodiment, the hexuronate C4-epimerase variant of the present invention may be a variant in which the threonine (T)-272 is substituted with aspartic acid (D), valine (V), isoleucine (I), leucine (L), methionine (M), glutamine (Q), or serine (S), the serine (S)-125 is substituted with aspartic acid (D), and the serine (S)-185 is substituted with lysine (K).

In an example of the exemplary embodiment, in the hexuronate C4-epimerase variant of the present invention, one or more amino acid residues selected from the group consisting of the valine (V)-267, the serine (S)-268, and the tryptophan (W)-306 from the N-terminal of the hexuronate C4-epimerase consisting of the amino acid sequence of SEQ ID NO: 1 are additionally mutated in addition to the threonine (T)-272, serine (S)-125, and serine (S)-185 amino acid residues. The variant may be a variant in which the valine (V)-267 is substituted with methionine (M), the serine (S)-268 is substituted with cysteine (C) or threonine (T), and the tryptophan (W)-306 is substituted with phenylalanine (F), histidine (H), methionine (M) or valine (V). In an exemplary embodiment, the hexuronate C4-epimerase variant of the present invention may be a variant in which the threonine (T)-272 is substituted with aspartic acid (D), valine (V), isoleucine (I), leucine (L), methionine (M), glutamine (Q), or serine (S), the serine (S)-125 is substituted with aspartic acid (D), the serine (S)-185 is substituted with lysine (K), and the valine (V)-267 is substituted with methionine (M). In an exemplary embodiment, the hexuronate C4-epimerase variant of the present invention may be a variant in which the threonine (T)-272 is substituted with aspartic acid (D), valine (V), isoleucine (I), leucine (L), methionine (M), glutamine (Q), or serine (S), the serine (S)-125 is substituted with aspartic acid (D), the serine (S)-185 is substituted with lysine (K), and the serine (S)-268 is substituted with cysteine (C) or threonine (T). In an exemplary embodiment, the hexuronate C4-epimerase variant of the present invention may be a variant in which the threonine (T)-272 is substituted with aspartic acid (D), valine (V), isoleucine (I), leucine (L), methionine (M), glutamine (Q), or serine (S), the serine (S)-125 is substituted with aspartic acid (D), the serine (S)-185 is substituted with lysine (K), and the tryptophan (W)-306 is substituted with phenylalanine (F), histidine (H), methionine (M) or valine (V). In an exemplary embodiment, the hexuronate C4-epimerase variant of the present invention may be a variant in which the threonine (T)-272 is substituted with aspartic acid (D), valine (V), isoleucine (I), leucine (L), methionine (M), glutamine (Q), or serine (S), the serine (S)-125 is substituted with aspartic acid (D), the serine (S)-185 is substituted with lysine (K), the valine (V)-267 is substituted with methionine (M), and the serine (S)-268 is substituted with cysteine (C) or threonine (T). In an exemplary embodiment, the hexuronate C4-epimerase variant of the present invention may be a variant in which the threonine (T)-272 is substituted with aspartic acid (D), valine (V), isoleucine (I), leucine (L), methionine (M), glutamine (Q), or serine (S), the serine (S)-125 is substituted with aspartic acid (D), the serine (S)-185 is substituted with lysine (K), the valine (V)-267 is substituted with methionine (M), and the tryptophan (W)-306 is substituted with phenylalanine (F), histidine (H), methionine (M) or valine (V). In an exemplary embodiment, the hexuronate C4-epimerase variant of the present invention may be a variant in which the threonine (T)-272 is substituted with aspartic acid (D), valine (V), isoleucine (I), leucine (L), methionine (M), glutamine (Q), or serine (S), the serine (S)-125 is substituted with aspartic acid (D), the serine (S)-185 is substituted with lysine (K), the serine (S)-268 is substituted with cysteine (C) or threonine (T), and the tryptophan (W)-306 is substituted with phenylalanine (F), histidine (H), methionine (M) or valine (V). In an exemplary embodiment, the hexuronate C4-epimerase variant of the present invention may be a variant in which the threonine (T)-272 is substituted with aspartic acid (D), valine (V), isoleucine (I), leucine (L), methionine (M), glutamine (Q), or serine (S), the serine (S)-125 is substituted with aspartic acid (D), the serine (S)-185 is substituted with lysine (K), the valine (V)-267 is substituted with methionine (M), the serine (S)-268 is substituted with cysteine (C) or threonine (T), and the tryptophan (W)-306 is substituted with phenylalanine (F), histidine (H), methionine (M) or valine (V).

In an exemplary embodiment, the hexuronate C4-epimerase variant of the present invention may be a variant in which the valine (V)-267 residue, the serine (S)-268 residue, or a combination of the valine (V)-267 residue and the serine (S)-268 residue is additionally mutated in addition to the threonine (T)-272 and serine (S)-125 residues. The valine (V)-267 residue may be substituted with methionine (M), and the serine (S)-268 may be substituted with cysteine (C) or threonine (T). In an exemplary embodiment, the hexuronate C4-epimerase variant of the present invention may be a variant in which the threonine (T)-272 is substituted with aspartic acid (D), valine (V), isoleucine (I), leucine (L), methionine (M), glutamine (Q), or serine (S), the serine (S)-125 is substituted with aspartic acid (D), the valine (V)-267 is substituted with methionine (M), and the serine (5)-268 is substituted with cysteine (C) or threonine (T).

In an exemplary embodiment, the hexuronate C4-epimerase variant of the present invention may be a variant in which aspartic acid (D)-231, the arginine (R)-386, or a combination thereof from the N-terminal of the hexuronate C4-epimerase consisting of the amino acid sequence of SEQ ID NO: 1 is additionally mutated in addition to the threonine (T)-272 and the serine (S)-125; and the valine (V)-267 and/or the serine (S)-268. The aspartic acid (D)-231 may be substituted with arginine (R), and the arginine (R)-386 may be substituted with proline (P) or valine (V). In an exemplary embodiment, the hexuronate C4-epimerase variant of the present invention may be a variant in which the threonine (T)-272 is substituted with aspartic acid (D), valine (V), isoleucine (I), leucine (L), methionine (M), glutamine (Q), or serine (S), the serine (S)-125 is substituted with aspartic acid (D), the valine (V)-267 is substituted with methionine (M), the serine (S)-268 is substituted with cysteine (C) or threonine (T), the aspartic acid (D)-231 is substituted with arginine (R), the arginine (R)-386 is substituted with proline (P) or valine (V), or both position Nos. 231 and 386 are substituted with arginine (R), or proline (P) or valine (V), respectively.

In an exemplary embodiment, the hexuronate C4-epimerase variant of the present invention may be variant in which one or more amino acid residues selected from the group consisting of the threonine (T)-97, the glutamine (Q)-149, the proline (P)-166, or the proline (P)-351 from the N-terminal of the hexuronate C4-epimerase consisting of the amino acid sequence of SEQ ID NO: 1 are additionally mutated in addition to the threonine (T)-272, the serine (S)-125, the valine (V)-267, the serine (S)-268, and the arginine (R)-386. The threonine (T)-97 may be substituted with alanine (A) or leucine (L), the glutamine (Q)-149 may be substituted with arginine (R), the proline (R)-166 may be substituted with arginine (R), and the proline (P)-351 may be substituted with serine (S). In an example of the exemplary embodiment, in the hexuronate C4-epimerase variant of the present invention, the threonine (T)-272 may be substituted with aspartic acid (D), valine (V), isoleucine (I), leucine (L), methionine (M), glutamine (Q), or serine (S), the serine (S)-125 may be substituted with aspartic acid (D), the valine (V)-267 may be substituted with methionine (M), the serine (S)-268 may be substituted with cysteine (C) or threonine (T), the arginine (R)-386 may be substituted with valine (V), or the threonine (T)-97 may be substituted with alanine (A) or leucine (L), or the glutamine (Q)-149 may be substituted with arginine (R), the proline (P)-166 may be substituted with arginine (R) or the proline (P)-351 may be substituted with serine (S).

In an exemplary embodiment, in the hexuronate C4-epimerase variant of the present invention, one or more amino acid residues selected from the group consisting of the lysine (K)-164, the aspartic acid (D)-168, and the glutamic acid (E)-175 from the N-terminal of the hexuronate C4-epimerase consisting of the amino acid sequence of SEQ ID NO: 1 may additionally be mutated in addition to the threonine (T)-272, serine (S)-125, and valine (V)-267 and/or serine (S)-268 amino acid residues. The lysine (K)-164 may be substituted with methionine (M), the aspartic acid (D)-168 may be substituted with glutamic acid (E), and the glutamic acid (E)-175 may be substituted with glycine (G).

According to another exemplary embodiment of the present invention, there is provided a hexuronate C4-epimerase variant in which a leucine (L)-77 amino acid residue from N-terminal of the hexuronate C4-epimerase consisting of an amino acid sequence of SEQ ID NO: 1 is mutated. The leucine (L)-77 may be substituted with proline (P) or arginine (R).

In an exemplary embodiment, in the hexuronate C4-epimerase variant of the present invention, the serine (S)-125 amino acid residue from the N-terminal of the hexuronate C4-epimerase consisting of the amino acid sequence of SEQ ID NO: 1 may additionally be mutated in addition to the leucine (L)-77 amino acid residue. The serine (S)-125 may be substituted with cysteine (C), tyrosine (Y), glutamine (Q), glutamic acid (E), threonine (T), asparagine (N), or aspartic acid (D).

In an exemplary embodiment, in the hexuronate C4-epimerase variant of the present invention, the alanine (A)-158, the proline (P)-351 or a combination of the amino acid residues from the N-terminal of the hexuronate C4-epimerase consisting of the amino acid sequence of SEQ ID NO: 1 may additionally be mutated in addition to the leucine (L)-77 and serine (S)-125 amino acid residues. The alanine (A)-158 may be substituted with threonine (T), and the proline (P)-351 may be substituted with serine (S).

In the hexuronate C4-epimerase variant of the present invention, one or more amino acid residues selected from the group consisting of the histidine (H)-9, the glutamic acid (E)-60, and the valine (V)-415 from the N-terminal of the hexuronate C4-epimerase consisting of the amino acid sequence of SEQ ID NO: 1 may additionally be mutated in addition to the leucine (L)-77, serine (S)-125, and alanine (A)-158 amino acid residues. Specifically, in the hexuronate C4-epimerase variant of the present invention, the leucine (L)-77, the serine (S)-125, the alanine (A)-158, the histidine (H)-9, the glutamic acid (E)-60, and valine (V)-415 amino acid residues may be mutated. The histidine (H)-9 may be substituted with tyrosine (Y), the glutamic acid (E)-60 may be aspartic acid (D), and the valine (V)-415 may be substituted with glutamic acid (E).

According to another exemplary embodiment of the present invention, there is provided a hexuronate C4-epimerase variant in which an alanine (A)-158 amino acid residue from N-terminal of the hexuronate C4-epimerase consisting of an amino acid sequence of SEQ ID NO: 1 is mutated. The alanine (A)-158 may be substituted with threonine (T).

In an exemplary embodiment, in the hexuronate C4-epimerase variant of the present invention, the serine (S)-125 amino acid residue from the N-terminal of the hexuronate C4-epimerase consisting of the amino acid sequence of SEQ ID NO: 1 may additionally be mutated in addition to the alanine (A)-158 amino acid residue. The serine (S)-125 may be substituted with cysteine (C), tyrosine (Y), glutamine (Q), glutamic acid (E), threonine (T), asparagine (N), or aspartic acid (D). In an example, in the amino acid sequence of SEQ ID NO: 1, the alanine (A)-158 may be substituted with threonine (T), and the serine (S)-125 may be substituted with cysteine (C), tyrosine (Y), glutamine (Q), glutamic acid (E), threonine (T), asparagine (N), or aspartic acid (D). In an exemplary embodiment, in the hexuronate C4-epimerase variant of the present invention, one or more amino acid residues selected from the group consisting of the glutamine (Q)-149, and the valine (V)-267 and the proline (P)-351 from the N-terminal of the hexuronate C4-epimerase consisting of the amino acid sequence of SEQ ID NO: 1 may additionally be mutated in addition to the alanine (A)-158 and serine (S)-125 amino acid residues. The glutamine (Q)-149 may be substituted with arginine (R), the valine (V)-267 may be substituted with methionine (M), and the proline (P)-351 may be substituted with serine (S). Accordingly, there may be provided variants in which the alanine (A)-158 amino acid residue is substituted with threonine (T), the serine (S)-125 is substituted with aspartic acid (D), and the glutamine (Q)-149 is additionally substituted with arginine (R) or the valine (V)-267 is substituted with methionine (M) or the proline (P)-351 is substituted with serine (S).

According to another exemplary embodiment of the present invention, there is provided a hexuronate C4-epimerase variant in which a proline (P)-351 amino acid residue from N-terminal of the hexuronate C4-epimerase consisting of an amino acid sequence of SEQ ID NO: 1 is mutated. The proline (P)-351 may be substituted with serine (S).

In an exemplary embodiment, in the hexuronate C4-epimerase variant of the present invention, the serine (S)-125 amino acid residue from the N-terminal of the hexuronate C4-epimerase consisting of the amino acid sequence of SEQ ID NO: 1 may additionally be mutated in addition to the proline (P)-351 amino acid residue. The serine (S)-125 may be substituted with cysteine (C), tyrosine (Y), glutamine (Q), glutamic acid (E), threonine (T), asparagine (N), or aspartic acid (D). Accordingly, there may be provided a variant in which the proline (P)-351 is substituted with serine (S) and the serine (S)-125 is substituted with cysteine (C), tyrosine (Y), glutamine (Q), glutamic acid (E), threonine (T), asparagine (N), or aspartic acid (D).

In an exemplary embodiment, in the hexuronate C4-epimerase variant of the present invention, the valine (V)-267 amino acid residue may additionally be mutated in addition to the proline (P)-351 and serine (S)-125 amino acid residues. The valine (V)-267 may be substituted with methionine (M). In the hexuronate C4-epimerase variant, one or more amino acid residues selected from the group consisting of the tyrosine (Y)-21, the valine (V)-62, the glutamine (Q)-149 and the leucine (L)-316 may additionally be mutated. The tyrosine (Y)-21 may be substituted with phenylalanine (F), the valine (V)-62 may be substituted with isoleucine (I), the glutamine (Q)-149 may be substituted with arginine (R), and the leucine (L)-316 may be substituted with phenylalanine (F). In an example of the exemplary embodiment, the variant may be a variant in which the proline (P)-351 is substituted with serine (S), the serine (S)-125 is substituted with aspartic acid (D), the valine (V)-267 is substituted with methionine (M), the tyrosine (Y)-21 is substituted with phenylalanine (F), the valine (V)-62 is substituted with isoleucine (I), and the glutamine (Q)-149 is substituted with arginine (R), and the leucine (L)-316 is substituted with phenylalanine (F).

Still another object of the present invention is to provide a hexuronate C4-epimerase variant in which a serine (S)-125 amino acid residue, a lysine (K)-164 amino acid residue, an aspartic acid (D)-168 amino acid residue, and a glutamic acid (E)-175 amino acid residue from N-terminal of a hexuronate C4-epimerase consisting of an amino acid sequence of SEQ ID NO: 1 are mutated. The serine (S)-125 may be substituted with cysteine (C), tyrosine (Y), glutamine (Q), glutamic acid (E), threonine (T), asparagine (N), or aspartic acid (D), the lysine (K)-164 may be substituted with methionine (M), the aspartic acid (D)-168 may be substituted with glutamic acid (E), and the glutamic acid (E)-175 may be substituted with glycine (G).

In an exemplary embodiment, in the hexuronate C4-epimerase variant in which the serine (S)-125, lysine (K)-164, aspartic acid (D)-168 and glutamic acid (E)-175 amino acid residues are mutated, one or more amino acid residues selected from the group consisting of leucine (L)-140, arginine (R)-386, serine (S)-268 and asparagine (N)-297 from the N-terminal of the hexuronate C4-epimerase consisting of the amino acid sequence of SEQ ID NO: 1 may additionally be mutated. The leucine (L)-140 may be substituted with proline (P), the arginine (R)-386 may be substituted with proline (P) or valine (V), the serine (S)-268 may be substituted with cysteine (C) or threonine (T), and the asparagine (N)-297 may be substituted with lysine (K). In an example of the exemplary embodiment, the variant may be a variant in which the serine (S)-125 is substituted with asoartic acid (D), the lysine (K)-164 is substituted with methionine (M), the aspartic acid (D)-168 is substituted with glutamic acid (E), the glutamic acid (E)-175 is substituted with glycine (G), the leucine (L)-140 is substituted with proline (P), and the arginine (R)-386 is substituted with proline (P). The hexuronate C4-epimerase variant of the present invention according to an example of the exemplary embodiment may be a variant in which the serine (S)-125 is substituted with aspartic acid (D), the lysine (K)-164 is substituted with methionine (M), the aspartic acid (D)-168 is substituted with glutamic acid (E), the glutamic acid (E)-175 is substituted with glycine (G), the serine (S)-268 is substituted with threonine (T), and the asparagine (N)-297 is substituted with lysine (K).

According to still another exemplary embodiment of the present invention, there is provided a hexuronate C4-epimerase variant in which serine (S)-125, glutamine (Q)-149, and valine (V)-267 amino acid residues from N-terminal of a hexuronate C4-epimerase consisting of an amino acid sequence of SEQ ID NO: 1 are mutated. The serine (S)-125 may be substituted with cysteine (C), tyrosine (Y), glutamine (Q), glutamic acid (E), threonine (T), asparagine (N), or aspartic acid (D), the glutamine (Q)-149 may be substituted with arginine (R), and the valine (V)-267 may be substituted with methionine (M).

According to an exemplary embodiment of the present invention, the hexuronate C4-epimerase variant of the present invention may include a polypeptide moiety having at least 50% genetic identity as compared to a hexuronate C4-epimerase variant consisting of an amino acid sequence (for example, an M125 variant in Tables 2 to 10) capable of being derived from mutated amino acid residue positions and substituted amino acid residues disclosed in Tables 2 to 9 in the amino acid sequence (SEQ ID NO: 1) of the wild-type hexuronate C4-epimerase, or a variant having the amino acid sequence, and according to an exemplary embodiment of the present invention, the hexuronate C4-epimerase variant of the present invention may include a polypeptide moiety having at least 60%, 70%, 75%, 80%, 85%, 90%, 95%, or 97% to 99% identity.

As used herein, the term "identity" refers to a percentage of identity between two polypeptide moieties. The correspondance between sequences from one moiety to another moiety may be determined by known techniques. For example, the identity may be determined by directly aligning sequence information between the two polypeptide molecules using a computer program in which the sequence information is aligned and readily available. Further, the identity may be determined by hybridization of the polynucleotide under a condition in which a stable double strand is formed between homologous regions, followed by degradation by a single-strand-specific nuclease to determine a size of the degraded fragment.

As used herein, all grammatical forms or spelling-modified forms of the term "identical" include superfamily derived proteins (e.g., immunoglobulin superfamily) and homologous proteins derived from other species (e.g., myosin light chain, etc.), and refer to a relationship between proteins having a "common evolutionary origin". The proteins (and coding genes thereof) have sequence identities that are reflected by a high degree of sequence similarity. However, the term "identical" in the general use and in the present invention refers to sequence similarity and does not mean a common evolutionary origin when referred to by an adjective such as "very high".

As used herein, the term "sequence similarity" refers to the degree of identity or correspondence between base sequences or amino acid sequences of a protein that may or may not share the common evolutionary origin. In an exemplary embodiment, when two amino acid sequences have at least 21% (at least about 50% in an embodiment, and at least 75%, 90%, 95%, 96%, 97% or 99% in another embodiment) of the polypeptide match with respect to a predetermined length of the amino acid sequence, they are "substantially identical" or "substantially similar". The substantially identical sequence may be identified by using standard software used in a data bank, or for example, by comparing sequences by Southern hybridization experiment under stringent conditions defined for a particular system. Appropriate hybridization conditions to be defined are within the range in the art (e.g., Sambrook et al., 1989, see infra).

The hexuronate C4-epimerase variants described herein have improved C4-epimerase unit activity in which D-fructose is converted into D-tagatose by epimerizing D-fructose at carbon number 4, thereby efficiently producing D-tagatose from D-fructose.

The hexuronate C4-epimerase variant of the present invention may be derived from hexuronate C4-epimerase of thermophilic microorganisms included in the genus *Rhodothermus*, the genus of *Thermoanaerobacter*, the genus of *Thermotoga*, or the genus of *Dictyoglomus*. Specifically, the variant may be derived from the hexuronate C4-epimerase of the genus *Thermotoga* microorganisms, and more specifically, may be derived from the hexuronate C4-epimerase of *Thermotoga neapolitana* or *Thermotoga maritima*.

The hexuronate C4-epimerase of the present invention may perform a stable reaction under the extreme reaction (high temperature, etc.) conditions while having the same function as the enzyme produced by mesophilic microorganisms (mesophile), and may have a number of advantages such as prevention of contamination against the mesophilic microorganisms, increase of solubility of materials having low solubility of substrate, and increase of reaction rate, etc. Thus, it is advantageous in that it is possible to overcome industrial disadvantages using the mesophilic enzyme.

The hexuronate C4-epimerase variants of the present invention may be obtained by transforming a strain such as *E. coli*, or the like, with DNA expressing the hexuronate C4-epimerase variant of the present invention, culturing the transformed strain to obtain a culture, crushing the culture, followed by purifying through a column, etc. Examples of the strain for the transformation include *Escherichia coli, Corynebacterium glutamicum, Aspergillus oryzae, Bacillus subtilis*, etc.

According to another exemplary embodiment of the present invention, the prevent invention provides a nucleic acid encoding a hexuronate C4-epimerase variant as described in the present invention, a transformant including the nucleic acid, or a composition for production of D-tagatose comprising a microorganism expressing the hexuronate C4-epimerase variant described in the present invention or a culture of the microorganism or the hexuronate C4-epimerase variant described in the present invention.

Another exemplary embodiment is directed to an expression vector including the nucleic acid encoding a hexuronate C4-epimerase variant described in the present invention.

The term "vector" in the present invention refers to any mediator for cloning and/or transferring of bases into an organism, such as a host cell. The vector may be a replicon that is able to bring the replication of combined fragments in which different DNA fragments are combined. Here, the term "replicon" refers to any genetic unit (e.g., plasmid, phage, cosmid, chromosome, virus) which functions as a self-unit of DNA replication in vivo, i.e., which is able to be replicated by self-regulation. The term "vector" includes viral and nonviral mediators for introducing the bases into the organism, e.g., a host cell, in vitro, ex vivo or in vivo. The term "vector" may also include mini-spherical DNA.

The term "nucleic acid" as used herein means that it encompasses DNA or RNA molecules, wherein nucleotides which are basic constituent units in the nucleic acid may include not only natural nucleotides but also analogues in which sugar or base sites are modified (see Scheit, Nucleotide Analogs, John Wiley, New York (1980); Uhlman and Peyman, Chemical Reviews, 90:543-584(1990)).

The term "transformation" as used herein means that the nucleic acid fragment migrates into the genome of a host organism to cause genetically stable transition, and the term "transformant" refers to an organism in which the genetically stable transition is caused by the migration of the nucleic acid in the genome thereof. The transformant may be, for example, a prokaryotic cell or a eukaryotic cell. Specifically, the transformant may be Enterobacteriaceae microorganism or coryneform microorganisms, etc., more specifically, the genus *Escherichia* microorganism, the genus *Serratia* microorganism, etc., and the most specifically, *E. coli*.

A method for transformation into an organism includes any method for introducing the nucleic acid into an organism and may be performed by appropriately selecting appropriate standard techniques as known in the art. As an example, the method includes electroporation, calcium phosphate co-precipitation, retroviral infection, microinjection, DEAE-dextran, cationic liposome method, etc., but is not limited thereto.

The composition for production of D-tagatose comprising a hexuronate C4-epimerase variant may further include any suitable excipient conventionally used in the composition for production of D-tagatose. The excipient may be, for example, but is not limited to, preservatives, wetting agents, dispersing agents, suspending agents, buffers, stabilizing agents, isotonic agents, or the like. The hexuronate C4-epimerase variant in the composition may be included in the range of 0.1 wt % to 70 wt % based on the solid weight of the composition.

According to still another exemplary embodiment of the present invention, the prevent invention provides a method for production of D-tagatose comprising: contacting the hexuronate C4-epimerase variant described in the present invention, the transformant described in the present invention, or the composition for production of tagatose described in the present invention with D-fructose to epimerize the D-fructose.

Hereinafter, the method for production of D-tagatose according to an exemplary embodiment of the present invention is described.

The method may include contacting the hexuronate C4-epimerase variant of the present invention, a microorganism expressing the variant or a culture of the microorganism or a composition for production of D-tagatose comprising the same with D-fructose. Thus, it is possible to epimerize D-fructose at carbon number 4.

Monosaccharides may be generally classified into aldohexose and ketohexose. D-fructose as a raw material in the present invention is an example of ketohexose, and the D-fructose may be used to produce D-tagatose.

The D-fructose may be produced by hydrolysis of sugar, or may be produced by isomerizing glucose. As a result, it is possible to produce tagatose at a high yield by using a universal and inexpensive raw material such as fructose, sugar and glucose, thereby enabling mass production of tagatose.

A step for epimerization of D-fructose of the present invention may be performed at a pH from 5 to 9, at a pH from 6 to 9, at a pH from 7 to 9, or at a pH from 7.5 to 8.5. The step for epimerization of D-fructose of the present invention may be performed at 50° C. to 85° C., 50° C. to 75° C. or 50° C. to 70° C. When treating the variant enzyme of the present invention under the above-described pH or temperature conditions, a reaction is able to proceed at a relatively high temperature, and thus, it is possible to minimize microbial contamination during the production process, to increase solubility of fructose used as a substrate, and to maximize a reaction rate and a conversion rate of the enzyme.

Further, the D-fructose of the present invention may have a concentration of 10 to 50% (w/v). According to an exemplary embodiment, the concentration may be 20 to 50% (w/v), 20 to 40% (w/v), 20 to 30% (w/v). The variant enzyme of the present invention is capable of producing D-tagatose from a high concentration of D-fructose, and thus is economically and efficiently capable of producing D-tagatose.

The step for epimerization of the D-fructose of the present invention may be performed in the presence of a metal salt. In an exemplary embodiment, a metal in the metal salt of the present invention may be at least one metal selected from the group consisting of Ni, Co, Mn, and Zn. Specifically, the metal salt of the present invention may be at least one selected from the group consisting of $NiSO_4$, $NiCl_2$, $CoCl_2$, $MnCl_2$, and $ZnSO_4$. Since the step for epimerization of D-fructose of the present invention is performed in the presence of the metal salt, an effect of improving the conversion activity is able to be obtained.

According to an exemplary embodiment of the present invention, the production method of the present invention may further include, before the contacting step of the present invention, hydrolyzing sugar to obtain D-fructose. The enzyme used for the hydrolysis may include at least one selected from the group consisting of β-D-fructosidase including β-fructofuranosidase, invertase, and saccharase, etc.; sucrase, α-glucosidase and α-D-glucohydrolase, but is not limited thereto.

According to an exemplary embodiment of the present invention, the production method of the present invention may further include, before the contacting step of the present invention, isomerizing glucose to obtain D-fructose. The isomerase may be glucose isomerase or phosphogluco isomerase, but is not limited thereto.

According to an exemplary embodiment of the present invention, the production method of the present invention may further include, after the contacting step of the present invention, obtaining an epimerization reaction product including D-tagatose.

According to an exemplary embodiment of the present invention, the production method of the present invention may further include, after the obtaining step of the epimerization reaction product of the present invention, purifying the obtained epimerization reaction product including D-tagatose.

According to an exemplary embodiment of the present invention, the production method of the present invention may further include, after the purifying step of the obtained epimerization reaction product of the present invention, crystallizing the purified epimerization reaction product including D-tagatose.

A method for purification of the epimerization reaction product is not particularly limited, and may be a method commonly used in the technical field of the present invention. Non-limiting examples thereof may include chromatography, fractional crystallization, ion purification, etc. The purification method may be performed only by one method, or by performing two or more methods together. For example, the epimerization reaction product may be purified through chromatography, and separation of the sugar by the chromatography may be performed by utilizing a difference in weak binding force between the sugar to be separated and the metal ion attached to an ion resin.

In addition, the present invention may further include performing decolorization, desalination or both of decolorization and desalination before or after the purification step of the present invention. By performing the decolorization and/or desalination, it is possible to obtain a more purified epimerization reaction product without impurities.

The purified epimerization reaction product may be concentrated to obtain a pure tagatose solution through an SMB chromatography process, followed by crystallization.

According to an exemplary embodiment of the present invention, the production method of the present invention may further include, before the crystallizing step of the present invention, concentrating the separated pure tagatose solution. The concentrating step may be performed to have a concentration of the epimerization reaction product including the purified D-tagatose about 2.5 to 3 times, and the crystallization may be performed more efficiently through the concentration step.

The method used in the crystallizing step of the present invention is not particularly limited, and may be a commonly used crystallization method. For example, a crystallization method using a cooling crystallization method may be used. Through the crystallizing step, it is possible to obtain finally purified D-tagatose at a high yield.

According to an exemplary embodiment of the present invention, the production method of the present invention may further include, after the purifying step of the present invention, reusing unreacted D-fructose in the contacting step of the present invention, or after the crystallizing step of the present invention, reusing a mother liquor from which a crystal is separated in the purifying step, or performing both steps. The reusing step is economically advantageous since D-tagatose may be obtained at a higher yield, and an amount of D-fructose to be discarded may be reduced.

The term "carbon number n" as used herein refers to a carbon position determined in accordance with carbon numbering prescribed in IUPAC nomenclature, and may be expressed as Cn. Here, n is an integer of 1 or more. For instance, "epimerization at carbon number 4" is represented by "C4-epimerization".

The amino acid residue (X) at the n-th position from the N-terminal of the hexuronate C4-epimerase consisting of the amino acid sequence of SEQ ID NO: 1 may be abbreviated as n X in the present invention.

In addition, it is possible to consider amino acids substitutable at the amino acid residues at corresponding positions mentioned in other parts of the present invention, unless otherwise stated herein with respect to amino acids which are substituted in the amino acid residues to be mutated in the present invention.

Amino acids in the present invention may be denoted by the following abbreviations or amino acid names.

TABLE 1

| Amino acid type | Abbreviation |
|---|---|
| Alanine | A |
| Arginine | R |
| Asparagine | N |
| Aspartic acid | D |
| Cysteine | C |
| Glutamic acid | E |
| Glutamine | Q |
| Glycine | G |
| Histidine | H |
| Isoleucine | I |
| Leucine | L |
| Lysine | K |
| Methionine | M |
| Phenylalanine | F |
| Proline | P |
| Serine | S |
| Threonine | T |
| Tryptophan | W |
| Tyrosine | Y |
| Valine | V |

In addition, the disclosures of Korean Patent Laid-Open Publication No. 10-2014-0143109 are incorporated herein by reference.

Advantageous Effects

The present invention provides a hexuronate C4-epimerase variant having improved activity of converting D-fructose into D-tagatose by epimerizing D-fructose at carbon number 4, thereby efficiently enabling mass-production of D-tagatose using D-fructose which is a universal raw material, and thus the production cost may be reduced to provide economic advantages.

Best Mode

Hereinafter, the present invention is described in more detail with reference to the following Examples. However, the following Examples are merely examples of the present invention, and the contents of the present invention should not be construed as being limited thereto.

EXAMPLE

Example 1. Improved Target Site Design and Analysis

Amino acids predicted to be functionally important were firstly selected based on analysis of the tertiary structure model of the active site of the ortholog (a homologous gene predicted to have the same function in different microbial species) which has identity with an amino acid of a hexuronate C4-epimerase derived from *Thermotoga neapolitana* (hereinafter referred to as wild-type). Then, based on analysis results of the docking model between D-fructose and the refined active site structure after the alanine scanning mutagenesis, a modified target site was designed for improvement of the unit activity of the conversion reaction of D-fructose by C4-epimerization. The details thereof are described as follows.

1-1. Ortholog Analysis

The homologous genes (ortholog) having identity with the wild-type amino acid sequence (SEQ ID NO: 1) [about 60 homologous genes with 80% sequence coverage and 50% or more homology] were screened using GenBank gene database. Through multiple sequence alignment analysis among amino acid sequences of the selected homologous genes, conserved amino acid residues predicted to be functionally important in the wild-type amino acid sequence were identified.

1-2. Analysis of Enzyme Tertiary Structure Model

There was no protein structure that appears to have 30% or more amino acid sequence identity with the homologous genes of the wild-type in Protein Data Bank database, and thus it was expected that accuracy in the prediction of the tertiary structure model of the wild-type by a homology modeling method would be low. Accordingly, the active sites among the tertiary structure models obtained from various modeling servers (RaptorX, Robetta, ModWeb, M4T, HHpred, PHYRE2, ITASSER and SWISS-MODEL) were compared and analyzed to obtain information about the structure sites that were predicted as the same.

1-3. Alanine Scanning Mutagenesis and Docking Binding Analysis

The amino acids that were selected based on the amino acid sequence analysis and the analysis of the tertiary structural model of the active site among the homologous genes as described above were substituted and mutated with alanine, and these recombinant mutation enzymes were produced in *Escherichia coli*. Then, characteristics of each mutation site were analyzed. Amino acids predicted to be functionally important were selected through the docking simulation between D-fructose and the refined active site structure after the alanine scanning mutagenesis was analyzed. Then, the modified target site was designed for the improvement of the unit activity of the conversion reaction of D-fructose by C4-epimerization. The amino acid sites of which activity is completely lost through the alanine scanning mutagenesis [assuming catalytic metal ion binding residues and deprotonation/protonation involved catalytic residues] were excluded from the target site for activity improvement.

Example 2. Production of Mutation Enzyme and Selection of Activity-Modified Mutation Enzyme Single-site saturation mutagenesis libraries of 54 target sites designed in Example 1 (amino acid residues at position Nos: 9, 21, 60, 62, 68, 77, 91, 97, 125, 126, 140, 141, 145, 149, 157, 158, 160, 163, 164, 166, 167, 168, 175, 176, 177, 185, 202, 218, 221, 231, 241, 242, 267, 268, 272, 276, 284, 295, 297, 302, 306, 316, 337, 351, 361, 366, 386, 388, 402, 403, 415, 429, 440, and 441 from the N-terminal of the wild-type hexuronate C4-epimerase) were constructed, and mutation sites of which the unit activity was improved and amino acids were screened. The multiple mutation enzyme was made by integrating the information of the screened modified sites to develop a mutation enzyme having improved unit activity of the conversion reaction of D-fructose by C4-epimerization.

2-1. Saturation Mutagenesis

The recombinant expression vector constructed for expression of wild-type enzyme gene, wild-type *Escherichia coli* BL21 (DE3) (which expresses the recombinant enzyme in which the wild-type was introduced into the NdeI and XhoI restriction enzyme sites of pET21a and 6xHis-tag is bound at the C-terminal of the wild-type) was used as a template for saturation mutagenesis for producing a variant library. Inverse PCR-based saturation mutagenesis was used in consideration of diversity of mutation distribution and yield of variants (2014. Anal. Biochem. 449: 90-98), NDT, VMA, ATG and TGG mixed primers in which termination codon was excluded and rare codons of *E. coli* were minimized in order to minimize the screening scale of the constructed variant library (i.e., to minimize the number of codons introduced during saturation mutagenesis) were designed and used (2012. Biotechniques 52:149-158). Specifically, a mixed primer including 15 bp for the front base, 3 bp (NDT, VMA, ATG and TGG, respectively) for substituting the displaced site, and 15 bp for the back base of the respective mutated sites, i.e., 33 bp in total length was constructed and used. The PCR was repeated 30 times under conditions of denaturation at 94° C. for 2 minutes, denaturation at 94° C. for 30 seconds, annealing at 60° C. for 30 seconds, extension at 72° C. for 10 minutes, and extension at 72° C. for 60 minutes. After constructing the saturation mutagenesis libraries for each mutation site, variants for each library were randomly selected (<mutation 11), and base sequences were analyzed to evaluate amino acid mutation distribution. Based on the analysis results, the screening scale of 90% or more of the sequence coverage for each library was determined (2003. Nucleic Acids Res. 15; 31:e30).

2-2. Screening of Activity-Modified Mutation Enzyme and Construction of Multiple Mutation Enzyme A chromogenic assay was used to specifically quantify D-fructose in order to rapidly screen large quantities of activity-modified mutation enzymes in the produced saturation mutagenesis libraries. Specifically, a 70% folin-ciocalteu reagent (SIGMA-ALDRICH) and a substrate reaction solution were mixed at a ratio of 15:1 and reacted at 80° C. for 5 minutes. The OD values measured at 900 nm were compared and analyzed.

54 variants in the mutation site with increased activity (D-tagatose production by conversion of D-fructose) as compared to the relative activity of the wild-type enzyme (SEQ ID NO: 1) were firstly selected. The base sequences of the corresponding genes were analyzed and the amino acid mutation information was analyzed (Tables 2 to 10).

The firstly selected mutation enzymes were reacted with D-fructose using a purified enzyme solution (His-tag affinity chromatography), and the reaction products were used to finally select 236 variants with the increased activity in producing D-tagatose by conversion from D-fructose as compared to the wild-type enzyme by using HPLC (column Shodex SUGAR SP-G, column analysis temperature of 80° C., mobile phase $H_2O$, flow rate of 0.6 ml/min, Refractive Index Detector).

Example 3. Comparative Evaluation of Activity-Modified Mutation Enzyme Characteristics In order to evaluate the relative activity of the D-fructose C4-epimerization on the mutation enzyme for a single site with improved unit activity and on the mutation enzyme for a multiple site in combination thereof, each enzyme was expressed in *E. coli* BL21 (DE3) by a conventional method (see Sambrook et al. 1989) and purified (by His-tag affinity chromatography). Then, in the presence of $NiSO_4$, each enzyme at a concentration of 10 units/ml was added to 25% (w/v) D-fructose substrate and reacted at pH 8.0 [50 mM potassium phosphate buffer] and at 65° C. for 2 hours, and the relative activity of D-fructose C4-epimerization as compared to the wild-type recombinase (wild-type, SEQ ID NO: 1) derived from *Thermotoga* neapolitana was measured.

TABLE 2

| name | 77 | 125 | 158 | 185 | 272 | 403 | Mutation Number | Relative Activity |
|---|---|---|---|---|---|---|---|---|
| WT | | | | | | | — | 100 |
| M1 | | C | | | | | 1 | 193 |
| M2 | | Y | | | | | 1 | 116 |
| M3 | | Q | | | | | 1 | 165 |
| M4 | | E | | | | | 1 | 202 |
| M5 | | T | | | | | 1 | 211 |
| M6 | | N | | | | | 1 | 131 |
| M7 | | D | | | | | 1 | 303 |
| M8 | | | | K | | | 1 | 114 |
| M9 | | | | R | | | 1 | 114 |
| M10 | | | | H | | | 1 | 118 |
| M11 | | | | Q | | | 1 | 107 |
| M12 | | | | A | | | 1 | 102 |
| M13 | | | | | F | | 1 | 104 |
| M14 | | | | | E | | 1 | 120 |
| M15 | | | | | D | | 1 | 121 |
| M16 | | | | | Q | | 1 | 116 |
| M17 | | | | | S | | 1 | 133 |
| M18 | | | | | V | | 1 | 117 |
| M19 | | | | | R | | 1 | 105 |
| M20 | | | | | K | | 1 | 117 |
| M21 | | | | | | S | 1 | 114 |
| M22 | | | | | | T | 1 | 130 |
| M23 | | | | | | Q | 1 | 119 |
| M24 | | | | | | F | 1 | 110 |
| M25 | | | | | | V | 1 | 117 |
| M26 | | | | | | I | 1 | 128 |
| M27 | | | | | | A | 1 | 119 |
| M28 | P | D | | | | | 2 | 479 |
| M29 | P | D | | | | | 2 | 487 |
| M30 | R | D | | | | | 2 | 426 |
| M31 | | D | T | | | | 2 | 494 |
| M32 | | D | | K | | | 2 | 543 |
| M33 | | D | | R | | | 2 | 430 |
| M34 | | D | | H | | | 2 | 493 |
| M35 | | D | | Q | | | 2 | 584 |
| M36 | | D | | A | | | 2 | 447 |

TABLE 3

| name | 77 | 125 | 149 | 158 | 185 | 267 | 268 | 272 | 351 | 403 | Mutation Number | Relative Activity |
|---|---|---|---|---|---|---|---|---|---|---|---|---|
| M37 | | D | | G | | | | | | | 2 | 481 |
| M38 | | D | | | | | | S | | | 2 | 355 |
| M39 | | D | | | | | | P | | | 2 | 199 |
| M40 | | D | | | | | | D | | | 2 | 343 |
| M41 | | D | | | | | | H | | | 2 | 259 |
| M42 | | D | | | | | | Q | | | 2 | 347 |
| M43 | | D | | | | | | N | | | 2 | 222 |
| M44 | | D | | | | | | K | | | 2 | 351 |
| M45 | | D | | | | | | H | | | 2 | 343 |
| M46 | | D | | | | | | Y | | | 2 | 305 |
| M47 | | D | | | | | | | S | | 2 | 421 |

TABLE 3-continued

| name | 77 | 125 | 149 | 158 | 185 | 267 | 268 | 272 | 351 | 403 | Mutation Number | Relative Activity |
|---|---|---|---|---|---|---|---|---|---|---|---|---|
| M48 |   | D |   |   |   |   |   |   |   | S | 2 | 377 |
| M49 |   | D |   |   |   |   |   |   |   | F | 2 | 380 |
| M50 |   | D |   |   |   |   |   |   |   | T | 2 | 431 |
| M51 |   | D |   |   |   |   |   |   |   | Q | 2 | 371 |
| M52 |   | D |   |   |   |   |   |   |   | V | 2 | 372 |
| M53 | R | D |   | T |   |   |   |   |   |   | 3 | 572 |
| M54 | P | D |   | T |   |   |   |   |   |   | 3 | 452 |
| M55 | P | D |   |   |   |   |   |   | S |   | 3 | 473 |
| M56 |   | D | R | T |   |   |   |   |   |   | 3 | 557 |
| M57 |   | D | R |   | M |   |   |   |   |   | 3 | 594 |
| M58 |   | D |   | T | M |   |   |   |   |   | 3 | 608 |
| M59 |   | D |   | T |   |   |   |   | S |   | 3 | 605 |
| M60 |   | D |   | T |   |   |   |   | S |   | 3 | 480 |
| M61 |   | D |   |   | Q |   | C |   |   |   | 3 | 422 |
| M62 |   | D |   |   | Q |   | C |   |   |   | 3 | 422 |
| M63 |   | D |   |   | K |   |   | D |   |   | 3 | 638 |
| M64 |   | D |   |   | K |   |   | V |   |   | 3 | 402 |
| M65 |   | D |   |   | K |   |   | I |   |   | 3 | 515 |
| M66 |   | D |   |   | K |   |   | L |   |   | 3 | 506 |
| M67 |   | D |   |   | K |   |   | M |   |   | 3 | 540 |
| M68 |   | D |   |   | K |   |   | Q |   |   | 3 | 628 |
| M69 |   | D |   |   | K |   |   |   | T |   | 3 | 790 |
| M70 |   | D |   |   | Q |   |   |   | T |   | 3 | 746 |
| M71 |   | D |   |   | M |   |   |   | S |   | 3 | 613 |
| M72 |   | D |   |   |   |   | D |   |   | F | 3 | 281 |
| M73 |   | D |   |   |   |   | D |   |   | S | 3 | 274 |
| M74 |   | D |   |   |   |   | D |   |   | V | 3 | 178 |
| M75 |   | D |   |   |   |   | D |   |   | I | 3 | 314 |

TABLE 4

| name | 9 | 21 | 60 | 62 | 68 | 77 | 97 | 125 | 140 | 149 | 158 | 164 | 166 | 168 | 175 | 185 | 231 | 267 | 268 | 272 | 297 | 306 | 316 | 351 | 386 | 403 | 415 | Mutation Number | Relative Activity |
|---|---|---|---|---|---|---|---|---|---|---|---|---|---|---|---|---|---|---|---|---|---|---|---|---|---|---|---|---|---|
| M76 |   |   |   |   |   | R |   | D |   |   | T |   |   |   |   |   |   |   |   |   |   |   |   |   |   | T |   | 4 | 441 |
| M77 |   |   |   |   |   |   |   | D |   |   |   |   |   |   |   |   |   |   | Q |   |   | H |   |   | M |   |   | 4 | 495 |
| M78 |   |   |   |   |   |   |   | D |   |   |   |   |   |   |   |   |   |   | Q |   |   | D |   |   | M |   |   | 4 | 548 |
| M79 |   |   |   |   |   | R |   | D |   |   | T |   |   |   |   |   |   |   |   |   |   |   |   |   |   | V | T | 5 | 437 |
| M80 |   |   |   |   |   |   |   | D |   |   |   |   |   |   |   |   |   |   | Q |   |   | C | D |   | M |   |   | 5 | 526 |
| M81 |   |   |   |   |   |   |   | D |   |   |   |   |   |   |   |   |   |   | Q | M | T | D |   |   |   |   |   | 5 | 451 |
| M82 |   |   |   |   |   |   |   | D |   |   |   |   |   |   | R |   |   |   | M | T | D |   |   |   |   |   |   | 5 | 510 |
| M83 |   |   |   |   |   |   |   | D |   |   |   |   |   |   |   |   |   |   | M | T | D |   |   |   | V |   |   | 5 | 555 |
| M84 |   |   |   |   |   |   |   | D |   |   |   |   |   |   |   |   |   |   | M |   |   |   |   | S | V | T |   | 5 | 445 |
| M85 | Y |   | D |   | P |   |   | D |   |   | T |   |   |   |   |   |   |   |   |   |   |   |   |   |   |   | E | 6 | 427 |
| M86 |   |   |   | G |   |   |   | D |   |   |   |   |   |   |   |   |   |   | Q | M |   |   |   |   |   | T |   | 6 | 489 |
| M87 |   |   |   |   |   | L |   | D |   |   |   |   |   |   |   |   |   |   | M | I | U |   |   |   | V |   |   | 6 | 695 |
| M88 |   |   |   |   |   |   |   | D | P |   |   | M |   | E | G |   |   |   |   |   |   |   |   |   | V |   |   | 6 | 564 |
| M89 |   |   |   |   |   |   |   | D |   |   |   |   | R |   |   |   |   |   | M | T | D |   |   |   | V |   |   | 6 | 496 |
| M90 |   |   |   |   |   |   |   | D |   |   |   | M |   | E | G |   |   |   |   | T |   | K |   |   |   |   |   | 6 | 498 |
| M91 |   |   |   |   |   |   |   | D |   |   |   |   | R |   |   |   |   |   | M | T | D |   |   |   | V |   |   | 6 | 592 |
| M92 |   |   |   |   |   |   |   | D |   |   |   |   |   |   |   |   |   | Q | M | T | D |   |   |   |   | T |   | 6 | 691 |
| M93 |   |   |   |   |   |   |   | D |   |   |   |   |   |   |   |   |   |   | M | T | D |   |   | S | V |   |   | 6 | 553 |
| M94 |   |   |   |   |   |   |   | D |   |   |   |   |   |   |   |   |   | Q | M | C | D |   | M |   |   |   |   | 6 | 588 |
| M95 |   | F |   | I |   |   |   | D |   |   |   |   |   |   |   |   | R |   | M |   |   |   | F | S |   |   |   | 7 | 540 |
| M96 |   | F |   | I |   |   |   | D |   |   |   |   |   |   |   |   | R |   | M |   |   |   | F | S |   |   |   | 7 | 454 |
| M97 |   | F |   | I |   |   |   | D |   |   |   |   |   |   |   |   | R |   | M |   |   |   | F | S |   |   |   | 7 | 498 |
| M98 |   | F |   | I |   |   |   | D |   |   |   |   |   |   |   |   | R |   | M |   |   |   | F | S |   |   |   | 7 | 500 |

TABLE 5

| name | 91 | 125 | 141 | 164 | 168 | 175 | 176 | 185 | 267 | 268 | 272 | 306 | 403 | Mutation Number | Relative Activity |
|---|---|---|---|---|---|---|---|---|---|---|---|---|---|---|---|
| M99 | W | D |   |   |   |   |   | Q | M | T | D |   | T | 7 | 478 |
| M100 | I | D |   |   |   |   |   | Q | M | T | D |   | T | 7 | 560 |
| M101 | N | D |   |   |   |   |   | Q | M | T | D |   | T | 7 | 486 |

TABLE 5-continued

| name | 91 | 125 | 141 | 164 | 168 | 175 | 176 | 185 | 267 | 268 | 272 | 306 | 403 | Mutation Number | Relative Activity |
|---|---|---|---|---|---|---|---|---|---|---|---|---|---|---|---|
| M102 |  | D | F |  |  |  |  | Q | M | T | D |  | T | 7 | 496 |
| M103 |  | D |  | M | E | G |  |  | M | C | D |  |  | 7 | 437 |
| M104 |  | D |  |  |  |  | H | Q | M | T | D |  | I | 7 | 610 |
| M105 |  | D |  |  |  | F |  | Q | M | T | D |  | I | 7 | 539 |
| M106 |  | D |  |  |  |  | Y | Q | M | T | D |  | I | 7 | 662 |
| M107 |  | D |  |  |  |  |  | Q | M | T | D | M | Q | 7 | 822 |
| M108 |  | D |  |  |  |  |  | Q | M | T | D | M | I | 7 | 1011 |
| M109 |  | D |  |  |  |  |  | Q | M | T | D | M | L | 7 | 728 |
| M110 |  | D |  |  |  |  |  | Q | M | T | D | M | A | 7 | 749 |
| M111 |  | D |  |  |  |  |  | Q | M | T | D | M | P | 7 | 728 |
| M112 |  | D |  |  |  |  |  | Q | M | T | D | M | V | 7 | 1023 |
| M113 |  | D |  |  |  |  |  | Q | M | T | D | M | W | 7 | 682 |
| M114 |  | D |  |  |  |  |  | Q | M | T | D | M | R | 7 | 607 |
| M115 |  | D |  |  |  |  |  | Q | M | T | D | M | H | 7 | 948 |
| M116 |  | D |  |  |  |  |  | Q | M | T | D | M | F | 7 | 956 |
| M117 |  | D |  |  |  |  |  | Q | M | T | D | M | K | 7 | 536 |
| M118 |  | D |  |  |  |  |  | Q | M | T | D | M | N | 7 | 932 |
| M119 |  | D |  |  |  |  |  | Q | M | T | D | M | E | 7 | 400 |
| M120 |  | D |  |  |  |  |  | Q | M | T | D | M | D | 7 | 476 |
| M121 |  | D |  |  |  |  |  | Q | M | T | D | M | C | 7 | 457 |
| M122 |  | D |  |  |  |  |  | Q | M | T | D | M | T | 7 | 690 |

TABLE 6

| name | 125 | 126 | 164 | 166 | 168 | 175 | 185 | 231 | 267 | 268 | 272 | 297 | 306 | 386 | 388 | 403 | Mutation Number | Relative Activity |
|---|---|---|---|---|---|---|---|---|---|---|---|---|---|---|---|---|---|---|
| M123 | D |  |  |  |  |  | Q |  | M | T | D |  | M | V |  |  | 7 | 326 |
| M124 | D |  |  |  |  |  | Q |  | M | T | D |  |  | V |  | T | 7 | 693 |
| M125 | D |  |  |  |  |  | Q |  | M | T |  |  | M | V |  | T | 7 | 822 |
| M126 | D |  |  |  |  |  | Q |  | M |  | D |  | M | V |  | T | 7 | 558 |
| M127 | D |  |  |  |  |  | Q |  |  | T | D |  | M | V |  | T | 7 | 655 |
| M128 | D |  |  |  |  |  |  |  | M | T | D |  | M | V |  | T | 7 | 597 |
| M129 |  |  |  |  |  |  | Q |  | M | T | D |  | M | V |  | T | 7 | 589 |
| M130 | D | G |  |  |  |  | Q |  | M | T | D |  |  | V |  | T | 8 | 521 |
| M131 | D |  | M |  | E | G |  |  |  | T |  | K |  |  | V | T | 8 | 445 |
| M132 | D |  |  | R |  |  | Q |  | M | T | D |  | M |  |  | T | 8 | 697 |
| M133 | D |  |  |  |  |  | Q | R | M | T | D |  | M |  |  | T | 8 | 640 |
| M134 | D |  |  |  |  |  | Q |  | M | T | D |  | M | V |  | M | 8 | 487 |
| M135 | D |  |  |  |  |  | Q |  | M | T | D |  | M | V |  | M | 8 | 786 |
| M136 | D |  |  |  |  |  | Q |  | M | T | D |  | M | V |  | G | 8 | 808 |
| M137 | D |  |  |  |  |  | Q |  | M | T | D |  | H | V |  | T | 8 | 440 |
| M138 | D |  |  |  |  |  | Q |  | M | T | D |  | V | V |  | T | 8 | 649 |
| M139 | D |  |  |  |  |  | Q |  | M | T | D |  | F | V |  | T | 8 | 740 |
| M140 | D |  |  |  |  |  | Q |  | M | T | D |  | M | V |  | I | 8 | 1006 |
| M141 | D |  |  |  |  |  | Q |  | M | T | V |  | M | V |  | I | 8 | 699 |
| M142 | D |  |  |  |  |  | Q |  | M | T | A |  | M | V |  | I | 8 | 540 |
| M143 | D |  |  |  |  |  | Q |  | M | C | D |  | M | V |  | T | 8 | 495 |
| M144 | D |  |  |  |  |  | Q |  | M | T | E |  | M | V |  | I | 8 | 931 |
| M145 | D |  |  |  |  |  | Q |  | M | T | D |  | M | V |  | G | 8 | 557 |
| M146 | D |  |  |  |  |  | Q |  | M | T | D |  | M | V |  | D | 8 | 625 |

TABLE 7

| name | 60 | 97 | 125 | 126 | 145 | 163 | 164 | 166 | 185 | 202 | 221 | 231 | 241 | 242 | 267 | 268 | 272 | 276 | 284 | 306 | 386 | 403 | 415 | Mutation Number | Relative Activity |
|---|---|---|---|---|---|---|---|---|---|---|---|---|---|---|---|---|---|---|---|---|---|---|---|---|---|
| M147 |  |  | D |  |  |  |  |  | Q |  |  |  |  |  | M | T | D |  |  | M | V | N |  | 8 | 408 |
| M148 |  |  | D |  |  |  |  |  |  |  |  |  |  |  | M | C | D |  | A | M |  | T | E | 8 | 418 |
| M149 | D |  | D |  |  |  | T | F |  |  |  |  | F |  | M | T |  |  |  |  | P | T |  | 9 | 643 |
| M150 |  | A | D |  |  |  |  |  | Q |  |  |  |  |  | M | T | D |  |  | M | V | T |  | 9 | 672 |
| M151 |  | L | D |  |  |  |  |  | Q |  |  |  |  |  | M | T | D |  |  | M | V | T |  | 9 | 695 |
| M152 |  |  | D | F |  |  |  |  | Q |  |  |  |  |  | M | T | D |  |  | M | V | T |  | 9 | 661 |
| M153 |  |  | D | L |  |  |  |  | Q |  |  |  |  |  | M | T | D |  |  | M | V | T |  | 9 | 656 |
| M154 |  |  | D | P |  |  |  |  | Q |  |  |  |  |  | M | T | D |  |  | M | V | T |  | 9 | 636 |
| M155 |  |  | D | I |  |  |  |  | Q |  |  |  |  |  | M | T | D |  |  | M | V | T |  | 9 | 667 |
| M156 |  |  | D | T |  |  |  |  | Q |  |  |  |  |  | M | T | D |  |  | M | V | T |  | 9 | 670 |
| M157 |  |  | D | A |  |  |  |  | Q |  |  |  |  |  | M | T | D |  |  | M | V | T |  | 9 | 518 |

TABLE 7-continued

| name | 60 | 97 | 125 | 126 | 145 | 163 | 164 | 166 | 185 | 202 | 221 | 231 | 241 | 242 | 267 | 268 | 272 | 276 | 284 | 306 | 386 | 403 | 415 | Mutation Number | Relative Activity |
|---|---|---|---|---|---|---|---|---|---|---|---|---|---|---|---|---|---|---|---|---|---|---|---|---|---|
| M158 |  | D | G |  |  |  |  |  | Q |  |  |  |  |  | M | T | D |  |  | M | V | I |  | 9 | 682 |
| M159 |  | D | R |  |  |  |  |  | Q |  |  |  |  |  | M | T | D |  |  | M | V | I |  | 9 | 553 |
| M160 |  | D |  | A |  |  |  |  | Q |  |  |  |  |  | M | T | D |  |  | M | V | T |  | 9 | 553 |
| M161 |  | D |  |  | A |  |  |  | Q |  |  |  |  |  | M | T | D |  |  | M | V | T |  | 9 | 664 |
| M162 |  | D |  |  |  | Q |  |  | Q |  |  |  |  |  | M | T | D |  |  | M | V | T |  | 9 | 597 |
| M163 |  | D |  |  |  |  | M |  | Q |  |  |  |  |  | M | T | D |  |  | M | V | T |  | 9 | 634 |
| M164 |  | D |  |  |  |  |  | R | Q |  |  |  |  |  | M | T | D |  |  | M | V | T |  | 9 | 752 |
| M165 |  | D |  |  |  |  |  |  | Q |  | R |  |  |  | M | T | D |  |  | M | V | T |  | 9 | 733 |
| M166 |  | D |  |  |  |  |  |  | Q |  |  | N |  |  | M | T | D |  |  | M | V | I |  | 9 | 699 |
| M167 |  | D |  |  |  |  |  |  | Q |  |  |  | T |  | M | T | D |  |  | M | V | I |  | 9 | 697 |
| M168 |  | D |  |  |  |  |  |  | Q |  |  |  |  | S | M | T | D |  |  | M | V | I |  | 9 | 736 |
| M169 |  | D |  |  |  |  |  |  | Q |  |  |  |  |  | M | T | D | E |  | M | V | I |  | 9 | 601 |
| M170 |  | D |  |  |  |  |  |  | Q |  |  |  |  |  | M | T | D |  | A | M | V | I |  | 9 | 586 |

TABLE 8

| name | 97 | 125 | 157 | 160 | 163 | 164 | 166 | 167 | 185 | 231 | 267 | 268 | 272 | 306 | 337 | 366 | 386 | 402 | 403 | 429 | 440 | Mutation Number | Relative Activity |
|---|---|---|---|---|---|---|---|---|---|---|---|---|---|---|---|---|---|---|---|---|---|---|---|
| M171 |  | D |  |  |  |  |  |  | Q |  | M | T | D | M | T |  | V |  | I |  |  | 9 | 1093 |
| M172 |  | D |  |  |  |  |  |  | Q |  | M | T | D | M | Y |  | V |  | I |  |  | 9 | 1093 |
| M173 |  | D |  |  |  |  |  |  | Q |  | M | T | D | M | N |  | V |  | I |  |  | 9 | 1489 |
| M174 |  | D |  |  |  |  |  |  | Q |  | M | T | D | M | P |  | V |  | I |  |  | 9 | 1408 |
| M175 |  | D |  |  |  |  |  |  | Q |  | M | T | D | M |  | S | V |  | I |  |  | 9 | 1180 |
| M176 |  | D |  |  |  |  |  |  | Q |  | M | T | D | M |  | S | V |  | I |  |  | 9 | 771 |
| M177 |  | D |  |  |  |  |  |  | Q |  | M | T | D | M |  | G | V |  | I |  |  | 9 | 367 |
| M178 |  | D |  |  |  |  |  |  | Q |  | M | T | D | M |  | C | V |  | I |  |  | 9 | 476 |
| M179 |  | D |  |  |  |  |  |  | Q |  | M | T | D | M |  |  | V | F | I |  |  | 9 | 677 |
| M180 |  | D |  |  |  |  |  |  | Q |  | M | T | D | M |  |  | V | C | I |  |  | 9 | 668 |
| M181 |  | D |  |  |  |  |  |  | Q |  | M | T | D | M |  |  | V | Y | I |  |  | 9 | 664 |
| M182 |  | D |  |  |  |  |  |  | Q |  | M | T | D | M |  |  | V |  | T | P |  | 9 | 585 |
| M183 |  | D |  |  |  |  |  |  | Q |  | M | T | D | M |  |  | V |  | T |  | A | 9 | 764 |
| M184 | L | D |  | M |  |  |  |  | Q |  | M | T | D | M |  |  | V |  | T |  |  | 10 | 550 |
| M185 | L | D |  |  | R |  |  |  | Q |  | M | T | D | M |  |  | V |  | T |  |  | 10 | 706 |
| M186 | L | D |  |  |  |  |  |  | Q | R | M | T | D | M |  |  | V |  | T |  |  | 10 | 613 |
| M187 |  | D | R |  |  |  |  |  | Q |  | M | T | D | M | W |  | V |  | I |  |  | 10 | 1268 |
| M188 |  | D |  | L |  |  |  |  | Q |  | M | T | D | M | W |  | V |  | I |  |  | 10 | 1429 |
| M189 |  | D |  | F |  |  |  |  | Q |  | M | T | D | M | W |  | V |  | I |  |  | 10 | 982 |
| M190 |  | D |  | R |  |  |  |  | Q |  | M | T | D | M | W |  | V |  | I |  |  | 10 | 565 |
| M191 |  | D |  | Y |  |  |  |  | Q |  | M | T | D | M | W |  | V |  | I |  |  | 10 | 668 |
| M192 |  | D |  | M |  |  |  |  | Q | R | M | T | D | M |  |  | V |  | T |  |  | 10 | 617 |
| M193 |  | D |  |  |  | A |  |  | Q |  | M | T | D | M | W |  | V |  | I |  |  | 10 | 1803 |
| M194 |  | D |  |  |  |  |  | W | Q |  | M | T | D | M | W |  | V |  | I |  |  | 10 | 1854 |

TABLE 9

| name | 125 | 167 | 177 | 185 | 218 | 267 | 268 | 272 | 295 | 306 | 337 | 386 | 403 | Mutation Number | Relative Activity |
|---|---|---|---|---|---|---|---|---|---|---|---|---|---|---|---|
| M195 | D | I |  | Q |  | M | T | D |  | M | W | V | I | 10 | 1678 |
| M196 | D | K |  | Q |  | M | T | D |  | M | W | V | I | 10 | 1432 |
| M197 | D | M |  | Q |  | M | T | D |  | M | W | V | I | 10 | 1770 |
| M198 | D | V |  | Q |  | M | T | D |  | M | W | V | I | 10 | 1351 |
| M199 | D | S |  | Q |  | M | T | D |  | M | W | V | I | 10 | 1951 |
| M200 | D |  | Y | Q |  | M | T | D |  | M | W | V | I | 10 | 911 |
| M201 | D |  | H | Q |  | M | T | D |  | M | W | V | I | 10 | 733 |
| M202 | D |  | L | Q |  | M | T | D |  | M | W | V | I | 10 | 1489 |
| M203 | D |  |  | Q | I | M | T | D |  | M | W | V | I | 10 | 818 |
| M204 | D |  |  | Q | S | M | T | D |  | M | W | V | I | 10 | 1294 |
| M205 | D |  |  | Q | L | M | T | D |  | M | W | V | I | 10 | 1348 |
| M206 | D |  |  | Q | F | M | T | D |  | M | W | V | I | 10 | 1350 |
| M207 | D |  |  | Q | C | M | T | D |  | M | W | V | I | 10 | 1204 |
| M208 | D |  |  | Q |  | M | T | D | C | M | W | V | I | 10 | 1000 |
| M209 | D |  |  | Q |  | M | T | D | R | M | W | V | I | 10 | 485 |
| M210 | D |  |  | Q |  | M | T | D | Y | M | W | V | I | 10 | 1261 |

TABLE 10

| name | 125 | 185 | 257 | 268 | 272 | 302 | 306 | 337 | 361 | 366 | 386 | 403 | 441 | Mutation Number | Relative Activity |
|---|---|---|---|---|---|---|---|---|---|---|---|---|---|---|---|
| M211 | D | Q | M | T | D | C | M | W |   |   | V | I |   | 10 | 1222 |
| M212 | D | Q | M | T | D |   | M | W | K |   | V | I |   | 10 | 966 |
| M213 | D | Q | M | T | D |   | M | W | E |   | V | I |   | 10 | 630 |
| M214 | D | Q | M | T | D |   | M | W | V |   | V | I |   | 10 | 586 |
| M215 | D | Q | M | T | D |   | M | W | W |   | V | I |   | 10 | 783 |
| M216 | D | Q | M | T | D |   | M | W | Y |   | V | I |   | 10 | 781 |
| M217 | D | Q | M | T | D |   | M | W | M |   | V | I |   | 10 | 549 |
| M218 | D | Q | M | T | D |   | M | W | R |   | V | I |   | 10 | 760 |
| M219 | D | Q | M | T | D |   | M | W | Q |   | V | I |   | 10 | 731 |
| M220 | D | Q | M | T | D |   | M | W | L |   | V | I |   | 10 | 638 |
| M221 | D | Q | M | T | D |   | M | W | R |   | V | I |   | 10 | 879 |
| M222 | D | Q | M | T | D |   | M | W | Y |   | V | I |   | 10 | 1428 |
| M223 | D | Q | M | T | D |   | M | W | C |   | V | I |   | 10 | 856 |
| M224 | D | Q | M | T | D |   | M | W | L |   | V | I |   | 10 | 589 |
| M225 | D | Q | M | T | D |   | M | F |   | S | V | I |   | 10 | 1306 |
| M226 | D | Q | M | T | D |   | M | E |   | S | V | I |   | 10 | 1246 |
| M227 | D | Q | M | T | D |   | M | S |   | S | V | I |   | 10 | 1271 |
| M228 | D | Q | M | T | D |   | M | W |   | S | V | I |   | 10 | 1306 |
| M229 | D | Q | M | T | D |   | M | W |   |   | V | I | E | 10 | 1160 |
| M230 | D | Q | M | T | D |   | M | W |   |   | V | I | W | 10 | 1150 |
| M231 | D | Q | M | T | D |   | M | W |   |   | V | I | H | 10 | 1250 |
| M232 | D | Q | M | T | D |   | M | W |   |   | V | I | K | 10 | 1270 |
| M233 | D | Q | M | T | D |   | M | W |   |   | V | I | A | 10 | 1250 |
| M234 | D | Q | M | T | D |   | M | W |   |   | V | I | R | 10 | 1220 |
| M235 | D | Q | M | T | D |   | M | W |   |   | V | I | S | 10 | 1449 |
| M236 | D | Q | M | T | D |   | M | W |   |   | V | I | F | 10 | 1294 |

From the above results, it could be confirmed that the C4-epimerase variants of the present invention had the increased D-fructose C4-epimerization activity as compared to that of the wild-type enzyme, and in particular, the enzyme variant of M199 was analyzed as having increased the unit activity about 20 times, and thus, it could be confirmed that the activity of producing tagatose of the present invention was remarkably increased as compared to the wild-type enzyme.

---

The invention claimed is:

1. A hexuronate C4-epimerase variant in which threonine (T) as an amino acid residue at a position corresponding to 272 from the N-terminus of a hexuronate C4-epimerase consisting of the amino acid sequence set forth in SEQ ID NO: 1 is mutated, and wherein the variant comprises an amino acid sequence having at least 80% sequence identity to the amino acid sequence of SEQ ID NO:1.

2. The hexuronate C4-epimerase variant according to claim 1, wherein the threonine (T) residue at a position corresponding to 272 is replaced by alanine (A), aspartic acid (D), glutamic acid (E), phenylalanine (F), glycine (G), histidine (H), isoleucine (I), lysine (K), leucine (L), methionine (M), asparagine (N), proline (P), glutamine (Q), arginine (R), serine (S), valine (V) or tyrosine (Y).

3. The hexuronate C4-epimerase variant according to claim 1, wherein the serine (S) residue at a position corresponding to 125 from the N-terminus of the hexuronate C4-epimerase is further mutated.

4. The hexuronate C4-epimerase variant according to claim 3, wherein the serine (S) residue at a position corresponding to 125 is replaced by cysteine (C), tyrosine (Y), glutamine (Q), glutamic acid (E), threonine (T), asparagine (N) or aspartic acid (D).

5. The hexuronate C4-epimerase variant according to claim 3, wherein (i) the serine (S) residue at a position corresponding to 185 or (ii) the valine (V) residue at a position corresponding to 267, the serine (S) residue at a position corresponding to 268 or a combination of the valine (V) residue at a position corresponding to 267 and the serine (S) residue at a position corresponding to 268 from the N-terminus of the hexuronate C4-epimerase is further mutated.

6. The hexuronate C4-epimerase variant according to claim 5, wherein the serine (S) residue at a position corresponding to 185 is replaced by alanine (A), glycine (G), histidine (H), lysine (K), glutamine (Q) or arginine (R).

7. The hexuronate C4-epimerase variant according to claim 5, wherein one or more amino acid residues selected from the group consisting of the valine (V) residue at a position corresponding to 267, the serine (S) residue at a position corresponding to 268, and the tryptophan (W) residue at a position corresponding to 306 from the N-terminus of the hexuronate C4-epimerase in addition to the serine (S) residue at a position corresponding to 185 are further mutated.

8. The hexuronate C4-epimerase variant according to claim 7, wherein the valine (V) residue at a position corresponding to 267 is replaced by methionine (M), the serine (S) residue at a position corresponding to 268 is replaced by cysteine (C) or threonine (T), and the tryptophan (W) residue at a position corresponding to 306 is replaced by phenylalanine (F), histidine (H), methionine (M) or valine (V).

9. The hexuronate C4-epimerase variant according to claim 5, wherein (i) the aspartic acid (D) residue at a position corresponding to 231, the arginine (R) residue at a position corresponding to 386 or a combination of the aspartic acid (D) residue at a position corresponding to 231 and the arginine (R) residue at a position corresponding to 386 from the N-terminus of the hexuronate C4-epimerase or (ii) one or more amino acid residues selected from the group consisting of the lysine (K) residue at a position corresponding to 164, the aspartic acid (D) residue at a position corresponding to 168, and the glutamic acid (E) residue at a position corresponding to 175 from the N-terminus of the hexuronate C4-epimerase in addition to the valine (V) residue at a position corresponding to 267, the serine (S) residue at a position corresponding to 268 or a combination of the valine (V) residue at a position corresponding to 267 and the serine (S) residue at a position corresponding to 268 are further mutated.

10. The hexuronate C4-epimerase variant according to claim 9, wherein the aspartic acid (D) residue at a position corresponding to 231 is replaced by arginine (R) and the arginine (R) residue at a position corresponding to 386 is replaced by proline (P) or valine (V).

11. The hexuronate C4-epimerase variant according to claim 9, wherein one or more amino acid residues selected from the group consisting of the threonine (T) residue at a position corresponding to 97, the glutamine (Q) residue at a position corresponding to 149, the proline (P) residue at a position corresponding to 166, and the proline (P) residue at a position corresponding to 351 from the N-terminus of the hexuronate C4-epimerase in addition to the valine (V) residue at a position corresponding to 267 and the arginine (R) residue at a position corresponding to 386 are further mutated.

12. The hexuronate C4-epimerase variant according to claim 11, wherein the threonine (T) residue at a position corresponding to 97 is replaced by alanine (A) or leucine (L), the glutamine (Q) residue at a position corresponding to 149 is replaced by arginine (R), the proline (P) residue at a position corresponding to 166 is replaced by arginine (R), and the proline (P) residue at a position corresponding to 351 is replaced by serine (S).

13. The hexuronate C4-epimerase variant according to claim 9, wherein the lysine (K) residue at a position corresponding to 164 is replaced by methionine (M), the aspartic acid (D) residue at a position corresponding to 168 is replaced by glutamic acid (E), and the glutamic acid (E) residue at a position corresponding to 175 is replaced by glycine (G).

14. A nucleic acid encoding the hexuronate C4-epimerase variant according to claim 1.

15. A method for D-tagatose production comprising bringing the hexuronate C4-epimerase variant according to claim 1 or a microorganism or a culture thereof expressing the variant into contact with D-fructose.

* * * * *

SEQUENCE LISTING

```
<160> NUMBER OF SEQ ID NOS: 1

<210> SEQ ID NO 1
<211> LENGTH: 481
<212> TYPE: PRT
<213> ORGANISM: Unknown
<220> FEATURE:
<223> OTHER INFORMATION: A wild type of Hexuronate C4-epimerase

<400> SEQUENCE: 1
```

Met Val Leu Lys Val Phe Lys Asp His Phe Gly Arg Gly Tyr Glu Val
 1               5                  10                  15

Tyr Glu Lys Ser Tyr Arg Glu Lys Asp Ser Leu Ser Phe Phe Leu Thr
                20                  25                  30

Lys Gly Glu Glu Gly Lys Ile Leu Val Val Ala Gly Glu Lys Ala Pro
            35                  40                  45

Glu Gly Leu Ser Phe Phe Lys Lys Gln Arg Val Glu Gly Val Ser Phe
        50                  55                  60

Phe Phe Cys Glu Arg Asn His Glu Asn Leu Glu Val Leu Arg Lys Tyr
65                  70                  75                  80

Phe Pro Asp Leu Lys Pro Val Arg Ala Gly Leu Arg Ala Ser Phe Gly
                85                  90                  95

Thr Gly Asp Arg Leu Gly Ile Thr Thr Pro Ala His Val Arg Ala Leu
            100                 105                 110

Lys Asp Ser Gly Leu Phe Pro Ile Phe Ala Gln Gln Ser Val Arg Glu
        115                 120                 125

Asn Glu Arg Thr Gly Arg Thr Trp Arg Asp Val Leu Asp Asp Ala Thr
    130                 135                 140

```
Trp Gly Val Phe Gln Glu Gly Tyr Ser Glu Gly Phe Gly Ala Asp Ala
145                 150                 155                 160

Asp His Val Lys Arg Pro Glu Asp Leu Val Ser Ala Ala Arg Glu Gly
                165                 170                 175

Phe Thr Met Phe Thr Ile Asp Pro Ser Asp His Val Arg Asn Leu Ser
            180                 185                 190

Lys Leu Ser Glu Arg Glu Lys Asn Glu Met Phe Glu Glu Ile Leu Lys
        195                 200                 205

Lys Glu Arg Ile Asp Arg Ile Tyr Leu Gly Lys Lys Tyr Thr Val Leu
    210                 215                 220

Gly Glu Arg Leu Glu Phe Asp Glu Lys Asn Leu Arg Asp Ala Ala Leu
225                 230                 235                 240

Val Tyr Tyr Asp Ala Ile Ala His Val Asp Met Met Tyr Gln Ile Leu
            245                 250                 255

Lys Asp Glu Thr Pro Asp Phe Asp Phe Glu Val Ser Val Asp Glu Thr
            260                 265                 270

Glu Thr Pro Thr Ser Pro Leu Phe His Ile Phe Val Val Glu Glu Leu
        275                 280                 285

Arg Arg Arg Gly Val Glu Phe Thr Asn Leu Ala Leu Arg Phe Ile Gly
        290                 295                 300

Glu Trp Glu Lys Gly Ile Asp Tyr Lys Gly Asp Leu Ala Gln Phe Glu
305                 310                 315                 320

Arg Glu Ile Lys Met His Ala Glu Ile Ala Arg Met Phe Glu Gly Tyr
            325                 330                 335

Lys Ile Ser Leu His Ser Gly Ser Asp Lys Phe Ser Val Tyr Pro Ala
            340                 345                 350

Phe Ala Ser Ala Thr Gly Gly Leu Phe His Val Lys Thr Ala Gly Thr
            355                 360                 365

Ser Tyr Leu Glu Ala Val Lys Val Ile Ser Met Val Asn Pro Glu Leu
    370                 375                 380

Phe Arg Glu Ile Tyr Arg Cys Ala Leu Asp His Phe Glu Glu Asp Arg
385                 390                 395                 400

Lys Ser Tyr His Ile Ser Ala Asp Leu Ser Lys Val Pro Glu Val Glu
            405                 410                 415

Lys Val Lys Asp Glu Asp Leu Pro Gly Leu Phe Glu Asp Ile Asn Val
            420                 425                 430

Arg Gln Leu Ile His Val Thr Tyr Gly Ser Val Leu Lys Asp Ala Ser
        435                 440                 445

Leu Lys Glu Arg Leu Phe Lys Thr Leu Glu Gln Asn Glu Glu Leu Phe
    450                 455                 460

Tyr Glu Thr Val Ala Lys His Ile Lys Arg His Val Asp Leu Leu Lys
465                 470                 475                 480

Gly
```